(12) United States Patent
Gertner et al.

(10) Patent No.: US 7,931,580 B2
(45) Date of Patent: Apr. 26, 2011

(54) METHODS AND DEVICES FOR PERCUTANEOUSLY MODIFYING ORGANS TO TREAT PATIENTS

(76) Inventors: Michael Gertner, Menlo Park, CA (US); Neil Sheehan, Atherton, CA (US); Robert Brommer, Fremont, CA (US)

( * ) Notice: Subject to any disclaimer, the term of this patent is extended or adjusted under 35 U.S.C. 154(b) by 1062 days.

(21) Appl. No.: 11/693,630

(22) Filed: Mar. 29, 2007

(65) Prior Publication Data

US 2007/0173888 A1    Jul. 26, 2007

Related U.S. Application Data

(63) Continuation of application No. 10/974,248, filed on Oct. 27, 2004, now Pat. No. 7,255,675.

(60) Provisional application No. 60/556,004, filed on Mar. 23, 2004, provisional application No. 60/584,219, filed on Jul. 1, 2004, provisional application No. 60/603,944, filed on Aug. 23, 2004.

(51) Int. Cl.
*A61F 2/00* (2006.01)
(52) U.S. Cl. .......................................................... 600/37
(58) Field of Classification Search ............... 600/29–31, 600/37; 128/898, DIG. 25; 607/40
See application file for complete search history.

(56) References Cited

U.S. PATENT DOCUMENTS

| | | | |
|---|---|---|---|
| 233,475 A | 10/1880 | Cook et al. | |
| 1,461,524 A | 7/1923 | Goddard | |
| 3,454,011 A * | 7/1969 | Wagner | 606/224 |
| 3,571,864 A | 3/1971 | Oger | |
| 3,664,345 A | 5/1972 | Dabbs et al. | |
| 4,060,089 A | 11/1977 | Noiles | |
| 4,246,893 A | 1/1981 | Berson | |
| 4,458,681 A | 7/1984 | Hopkins | |
| 4,558,699 A | 12/1985 | Bashour | |
| 4,669,473 A | 6/1987 | Richards et al. | |
| 4,705,040 A | 11/1987 | Mueller et al. | |
| 4,803,985 A | 2/1989 | Hill | |
| RE34,021 E * | 8/1992 | Mueller | 600/37 |
| 5,151,086 A * | 9/1992 | Duh et al. | 604/506 |
| 5,234,454 A | 8/1993 | Bangs | |
| 5,258,015 A * | 11/1993 | Li et al. | 606/232 |
| 5,259,399 A | 11/1993 | Brown | |
| 5,549,621 A | 8/1996 | Bessler et al. | |
| 5,626,614 A * | 5/1997 | Hart | 606/232 |
| 5,951,590 A * | 9/1999 | Goldfarb | 606/232 |
| 5,961,440 A * | 10/1999 | Schweich et al. | 600/16 |
| 5,993,473 A | 11/1999 | Chan et al. | |

(Continued)

FOREIGN PATENT DOCUMENTS

WO      WO 99/25418        5/1999

(Continued)

OTHER PUBLICATIONS

Buchwald, et al., "Evolution of Operative Procedures for the Management of Morbid Obesity 1950-2000", *Obesity Surgery*, (2003) 12:705-717.

(Continued)

*Primary Examiner* — Samuel G Gilbert

(57) ABSTRACT

Disclosed are methods and apparatus for implantation into the walls of an organ such as the stomach. Deformable or inflatable anchors with a connector between are used to pull the walls of the organ together, or to implant devices in the wall of the organ. Also disclosed are surgical instruments useful in practicing the disclosed methods.

27 Claims, 20 Drawing Sheets

U.S. PATENT DOCUMENTS

| | | |
|---|---|---|
| 6,113,609 A | 9/2000 | Adams |
| 6,454,785 B2 | 9/2002 | De Hoyos Garza |
| 6,535,764 B2 | 3/2003 | Imran et al. |
| 6,558,400 B2 | 5/2003 | Deem et al. |
| 6,656,182 B1 | 12/2003 | Hayhurst |
| 6,699,260 B2 * | 3/2004 | Dubrul et al. ............... 606/200 |
| 2001/0010005 A1 | 7/2001 | Kammerer et al. |
| 2002/0055757 A1 | 5/2002 | Torre et al. |
| 2003/0055463 A1 | 3/2003 | Gordon et al. |
| 2003/0130669 A1 * | 7/2003 | Damarati ............... 606/151 |
| 2004/0006351 A1 | 1/2004 | Gannoe et al. |
| 2004/0024386 A1 | 2/2004 | Deem et al. |
| 2004/0097986 A1 | 5/2004 | Adams et al. |
| 2004/0116949 A1 | 6/2004 | Ewers et al. |
| 2004/0122456 A1 | 6/2004 | Saadat et al. |
| 2004/0122473 A1 | 6/2004 | Ewers |
| 2006/0265042 A1 | 11/2006 | Catanese, III et al. |
| 2006/0276871 A1 | 12/2006 | Lamson et al. |

FOREIGN PATENT DOCUMENTS

| | | |
|---|---|---|
| WO | WO 03/095015 | 11/2003 |
| WO | WO 2004/004542 | 1/2004 |
| WO | WO 2004/014237 | 2/2004 |
| WO | WO 2004/019765 | 3/2004 |
| WO | WO 2004/021894 | 3/2004 |
| WO | WO 2005/018417 | 3/2005 |
| WO | WO 2006/127431 | 11/2006 |

OTHER PUBLICATIONS

Cope, et al., "Percutaneous Transgastric Technique for Creating Gastroenteric Anastomoses in Swine", *Journal of Vascular and Interventional Radiology*, (2004) 15:177-181.

Cummings, et al., "Genetics and Pathophysiology of Human Obesity", *An Annual Review of Medicine*, (2003) 64:453-471.

Johnston, et al., "The Magenstrasse and Mill Operation for Morbid Obesity", *Obesity Surgery*, (2003) 13:10-16.

Roman, et al., "Intragastric Balloon for 'Non-Morbid' Obesity: A Retrospective Evaluation of Tolerance and Efficacy", Obesity Surgery, (2004) 14:539-544.

Sjostrom, et al., "Lifestyle, Diabeter, and Cardiovascular Risk Factors 10 Years After Bariatric Surgery", New England Journal of Medicine, (2004) 351(26):2683-2693.

Smith, et al., "Results and Complications of Gastric Partitioning: Four Year Follow-Up of 300 Morbidly Obese Patients", *The American Journal of Surgery*, (1983) 146:815-819.

\* cited by examiner

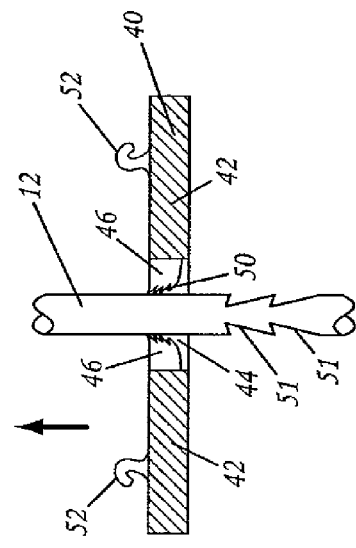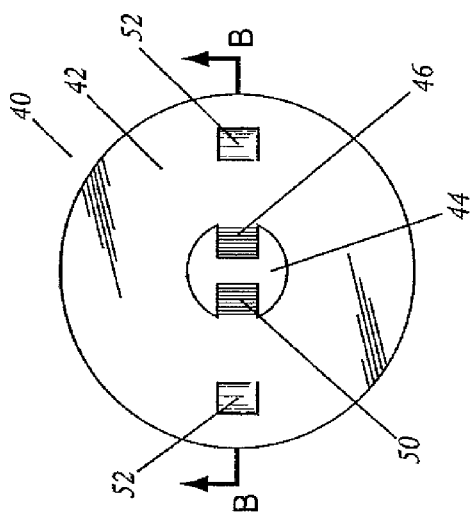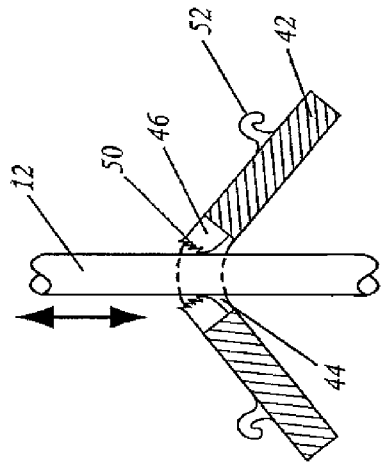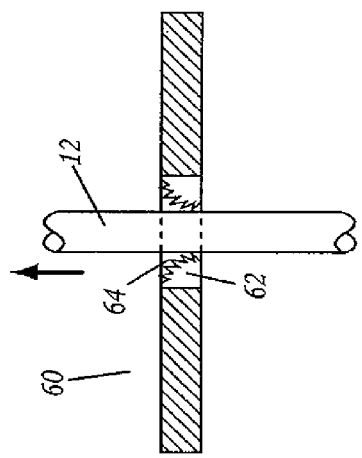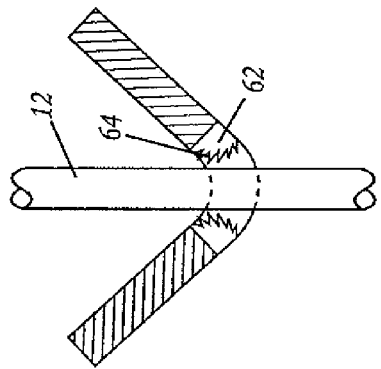
FIG. 2B
FIG. 2C
FIG. 2D
FIG. 2E
FIG. 2F

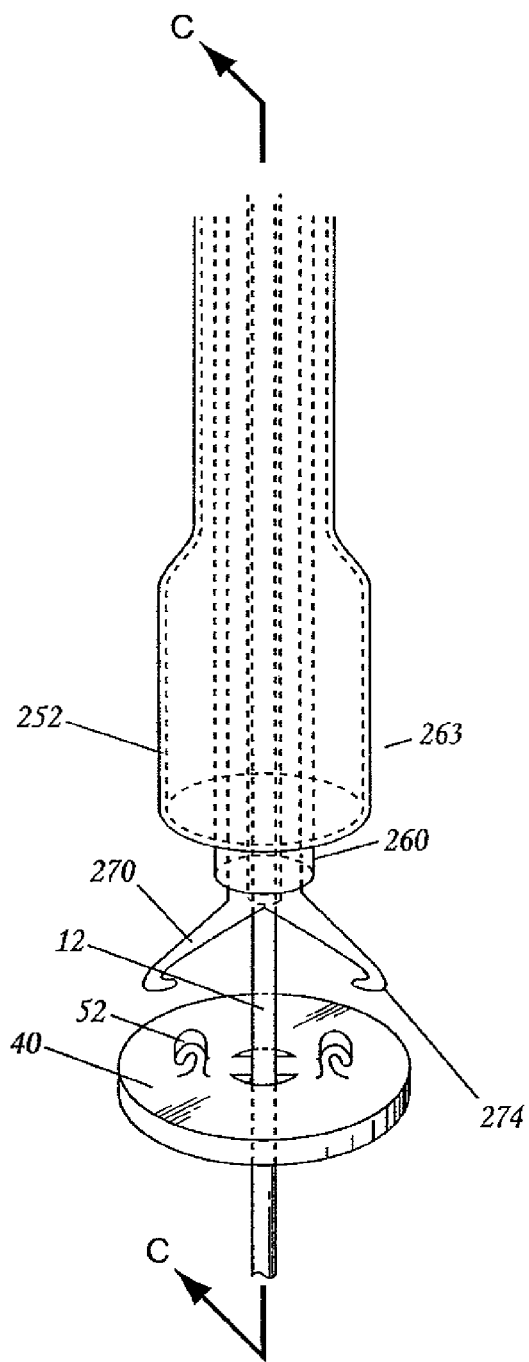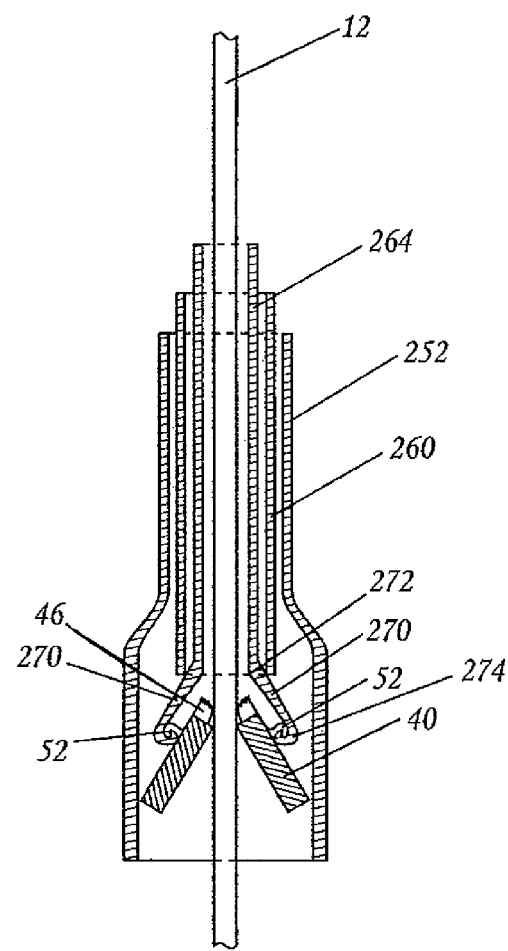
FIG. 5B                    FIG. 5C

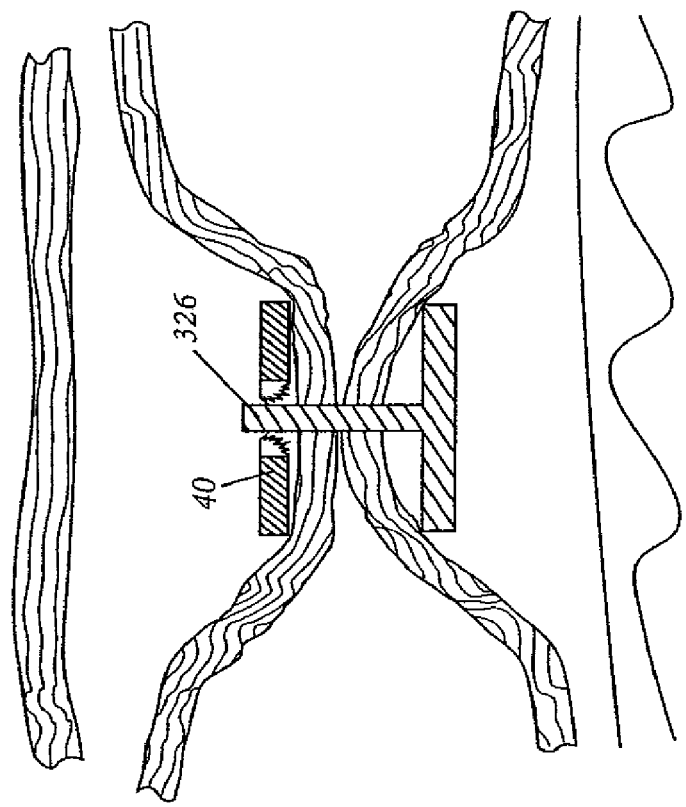
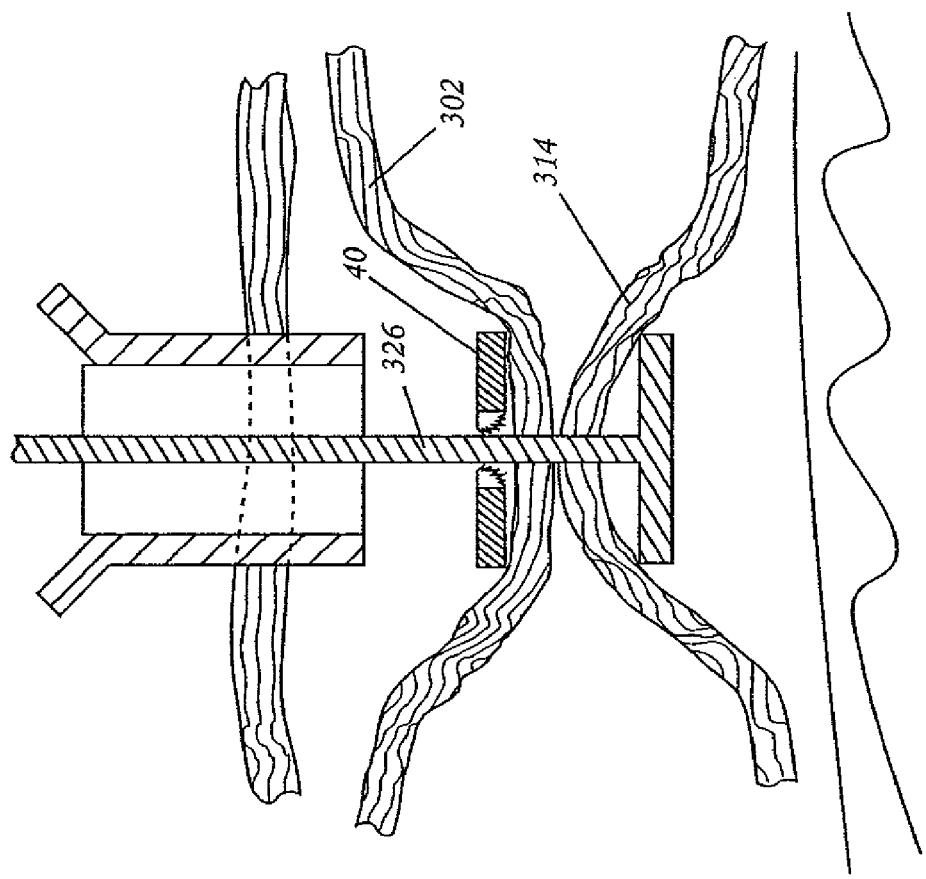
FIG. 7B
FIG. 7C

METHODS AND DEVICES FOR PERCUTANEOUSLY MODIFYING ORGANS TO TREAT PATIENTS

RELATED APPLICATION

The present application is a continuation of U.S. patent application Ser. No. 10/974,248 filed Oct. 27, 2004, which claims priority to U.S. Provisional Patent Application Ser. No. 60/556,004 filed Mar. 23, 2004 by Michael Gertner, M.D., entitled "BARIATRIC DEVICES AND IMPLANTATION METHODS," to U.S. Provisional Patent Application Ser. No. 60/584,219 filed Jul. 1, 2004 by Michael Gertner, M.D., entitled "DEVICES AND METHODS FOR PERCUTANEOUS GASTROPLASTY," and to U.S. Provisional Patent Application Ser. No. 60/603,944 filed Aug. 23, 2004 by Michael Gertner, M.D., entitled "DEVICES AND METHODS TO TREAT MORBID OBESITY," all of which are herein incorporated by reference in their entirety.

BACKGROUND OF THE INVENTION

1. Field of the Invention

The present invention relates to methods and apparatus for implanting devices in the wall of a hollow organ, including devices to reduce the volume of the stomach.

2. Description of the Related Art

Obesity is a public health problem of growing national and international importance. There are an estimated 60 million obese adults and 2 million obese adolescents in the United States as of 2004. By some estimates, there are 1 billion obese individuals worldwide.

Over the past four decades, there have been numerous surgical procedures and devices developed to treat the morbidly obese. In general, there are two physiologic aspects of all past and current procedures: malabsorption and mechanical restriction/volume reduction.

Many of the procedures performed in the past have proven to be impractical, dangerous, or detrimental to the health of the patients and are now of historical importance only. An example of a failed procedure is the jejunal-ileo bypass in which a malabsorptive state is created through the bypass of a large portion of the intestine through the creation of a surgical anastamosis between the jejunum and the ileum. While patients initially lost a great deal of weight, liver failure or liver damage occurred in over one-third of the patients which necessitated reversal of the surgical procedure.

The Roux-en-Y (The Roux) bypass operation has evolved to become the most commonly performed surgical procedure to treat the morbidly obese. It combines a small degree of malabsorption with a 90% reduction in the volume of the stomach. In the United States, 150,000 procedures are predicted for the year 2004. This number is expected to rise to 500,000 procedures by 2006. The procedure has been performed since the late 1970's and the long-term data has been very good. The advent of laparoscopic surgery and hence the laparoscopic Roux-en-Y bypass in combination with excellent follow-up results from the open procedure are reasons for the proliferation of the Roux procedure.

Despite the efficacy of the Roux procedure and the recent laparoscopic improvements, it remains a highly invasive procedure with substantial morbidity including a 1-2% surgical mortality, a 20-30% incidence of pulmonary morbidity such as pneumonia, pulmonary embolism, etc., and a 1-4% chance of leak at the anastamotic site which can result in a spectrum of consequences including an extended hospital stay to death.

The Roux procedure requires general anesthesia and muscle paralysis which, in the morbidly obese population, is not of small consequence. There is also a substantial rate of anastamotic stricture which results in severe lifestyle changes for patients. For example, many patients are forced to vomit after meals.

The largest problem from the perspective of the patient is that the Roux-en-Y is not reversible, which dramatically limits the number of patients willing to undergo the procedure. In particular, it severely limits the number of procedures which can or should be performed on adolescents.

The Magenstrasse and Mill (M&M) procedure is an evolving technique wherein the greater curvature of the stomach is essentially taken out of the path of food, leaving a tube of stomach, the Magenstrasse, or street of the stomach, comprised of the lesser curvature. The antrum is preserved in this procedure. The theory behind leaving the antral "mill" is that it will continue to serve its normal function of mixing, grinding, retropulsion, and well-regulated expulsion of chyme into the duodenum. An authoritative study on the operation is incorporated herein by reference (Johnston et. al. The Magenstrasse and Mill Operation for Morbid Obesity; Obesity Surgery 13, 10-16).

Percutaneous Endoscopic Gastrostomy (PEG) refers to a procedure in which a gastrocutaneous tract is created using percutaneous means. A recent update of the procedure can be found on the Society of American Gastrointestinal Endoscopic Surgeons (SAGES) website, and is incorporated herein by reference. Briefly, the procedure involves insufflation of the stomach with and under visualization with an endoscope. A small incision is made in the skin and a needle is advanced into the stomach (the stomach sits just under the abdominal wall when insufflated) under endoscopic visualization. A feeding tube is then placed over the needle to create a gastrocutaneous tract with the feeding tube inside the tract. The feeding tube is secured with an external bolster. Over the ensuing weeks, a permanent tract evolves between the stomach mucosa and epithelium of the skin, after which, the bolster can be removed without consequence. When the feeding tube is to be removed, the gastrocutaneous tract will closet on its own as food will preferentially be delivered antegrade (the path of least resistance) to the duodenum, thereby allowing the tract to heal.

Recently, minimally invasive procedures and devices which create a feeling of early satiety have been introduced into the marketplace. The LAP-BAND™ is a band which encircles the stomach at the region of the fundus-cardia junction. It requires general anesthesia, a pneumoperitoneum, muscle paralysis, and extensive dissection of the stomach at the level the gastroesophageal junction. Although less invasive than the Roux procedure and potentially reversible, the LAP-BAND™ is nonetheless quite invasive. It also does not reduce the volume of the stomach and patients report a feeling of hunger much of the time.

More recently, there has been an effort to develop even less invasive devices and procedures which do not involve incisions at all. For the most part, these procedures are performed from within the stomach with an endoscope and by a physician with a high degree of endoscopic skill. For example, U.S. Pat. No. 6,558,400 describes methods and devices to create partitions in the stomach. Fasteners or staplers applied through an endoscope from within the stomach are used to accomplish the partitions. Similarly, U.S. Patent Application Publication No. 2004/0122456 describes another set of methods and devices to reduce the volume of the stomach. Expandable anchors are deployed both on the anterior and posterior wall of the stomach by way of an endoscope. Flexible sutures are brought out of the patient's mouth and the sutures are crimped together within the stomach in order to bring the walls of the stomach closer together. Patent application WO2004/004542 describes a device which is advanced through an endoscope and grasps or applies suction to a fold of mucosa to apply fasteners through the mucosal and serosal layers of the stomach.

Endoscopic procedures to manipulate the stomach are time consuming because of the technical difficulty of the endoscopy; they also require a large endoscope through which many instruments need to be placed for these complex procedures. Due to the large girth of the endoscope, patients typically will require general anesthesia, limiting the "non-invasive" aspects of the procedure. Furthermore, the procedures require advanced endoscopic skill which would need to be acquired by most practitioners. Such skill adaptation can take a significant amount of time, which will limit adoption of the procedure by the physician community. A further issue is that there is a limitation on the size of the anchors which can be placed because the endoscope has a maximum size.

SUMMARY OF THE INVENTION

One embodiment of the present invention is a method for reducing the interior volume of an organ comprising passing a first end of a first surgical instrument through the patient's skin, through a first exterior surface of the organ, through the interior of the organ, and then through a second exterior surface of the organ, so that the surgical instrument traverses the organ, deploying a first anchor from the surgical instrument wherein the first anchor is located adjacent to the second exterior surface of the organ, partially or completely withdrawing the surgical instrument, deploying a second anchor wherein the second anchor is located adjacent to the first exterior surface of the organ, providing a connector between the first and second anchors, wherein the length of the connector between the first and second anchors is such that the first and second anchors urge the first and second exterior surfaces of the organ toward each other, thereby reducing the volume of the organ. In some embodiments, the first and second anchors are deployed from the same surgical instrument. Another aspect of the invention is a method of reversing the volume reducing procedure by cutting or otherwise dividing the one or more connectors between the first and second anchors. In another embodiment of the method, the organ is a gastrointestinal organ. The method may further comprise creating a space outside the organ adjacent to the second exterior surface thereof by introducing a volume-filling substance into a potential space adjoining the second exterior surface. The potential space can be expanded by the injection of a gas, liquid, gel, foam, or solid, into the potential space, by the inflation of a balloon placed in the potential space, or by blunt dissection. The method may further comprise insufflating the organ prior to the passing of the first end of a surgical instrument through a first exterior surface of the organ. In some embodiments, the patient's skin is overlying the patient's stomach, the organ is the patient's stomach, the first exterior surface is the anterior wall of the stomach, the second exterior surface is the posterior wall of the stomach, and the potential space is the lesser sac of the peritoneum. The method may further comprise urging the anterior and posterior walls of the stomach closer together by shortening the length of the connector between the first and the second anchors. In some embodiments, the surgical instrument is inserted into the patient's abdomen by directly penetrating the patient's skin and abdominal wall, by passing the surgical instrument through a laparoscopic port, or by passing the surgical instrument through an incision in the patient's skin and abdominal wall.

Another embodiment of the invention is a method for reducing the volume of a patient's stomach, comprising passing a first anchor through a patient's abdominal skin, and through the patient's anterior and posterior stomach walls, wherein the first anchor is in a reduced profile configuration, passing a second anchor through a patient's abdominal skin and adjacent to the patient's anterior stomach wall, connecting the first and second anchors by means of a connector that passes through the stomach, urging the first and second anchors toward each other, and holding the anterior and posterior walls of the stomach together with the first and second anchors, wherein the first anchor is in a deployed configuration and the connector prevents the first and second anchors from moving apart. Some embodiments further comprise passing the second anchor through the patient's abdominal skin while the second anchor is in a reduced profile configuration, as well as the second anchor subsequently being in a deployed configuration. In some embodiments, the holding of the anterior and posterior walls of the stomach together is performed in a manner that permits some space between mucosal surfaces of the stomach interior of the walls. In other embodiments it is performed in a manner that permits contact between mucosal surfaces of the stomach interior of the walls. In some embodiments, the holding step is performed by adjusting the relative position of the connector and the second anchor, and then configuring the second anchor to engage the connector in a manner that prevents the first and second anchors from moving apart.

Another embodiment of the invention is a fastening assembly, comprising a first anchor, a second anchor, and a connector, wherein the first anchor comprises a relatively planar body attached to the connector, the body of the first anchor having a relatively planar deployed profile and a reduced profile configuration, wherein the second anchor comprises a relatively planar body, a hole or other passageway approximately in the center of the body of sufficient diameter to allow passage of the connector through the hole or other passageway, one, two or more gripping elements projecting into the hole or other passageway, and one, two or more attachment structures accessible from a top surface of the body, the body of the second anchor having a relatively planar deployed profile and a reduced profile configuration, and wherein the gripping elements prevent movement of the second anchor along the longitudinal axis of the connector in the direction away from the first anchor when the connector is disposed in the hole or other passageway when the second anchor is in its deployed configuration.

Another embodiment of the invention is a biocompatible surgical anchor adapted for use in connecting the walls of a hollow organ or anchoring a device to the wall of a hollow organ, comprising a body portion, wherein the body portion is compressible and can assume a relatively planar deployed configuration and a reduced-profile compressed configuration, wherein the body portion has an opening extending therethrough, and a gripper on the body portion adapted to grip an elongated connector as such a connector extends through the opening, wherein the gripper engages such a connector when the anchor is in the deployed configuration, and releases such a connector when the anchor is in the compressed configuration. In some embodiments, the body portion is inflatable and can assume a relatively planar deployed configuration when inflated and a reduced-profile configuration when uninflated, wherein the body portion has an opening extending therethrough, and a gripper on the body portion adapted to grip an elongated connector as such a connector extends through the opening, wherein the gripper engages such a connector when the anchor is inflated, and releases such a connector when the anchor is uninflated.

Another embodiment of the invention is a fastening assembly, comprising a first anchor, a second anchor, and a connector, wherein the first anchor comprises an inflatable body attached to the connector, the body of the first anchor having a deployed configuration when inflated that is relatively spherical and a reduced profile configuration when uninflated wherein it is readily deformable, wherein the connector is hollow and configured to allow inflation of the first anchor by delivery of a filling substance through the connector to the first anchor.

Another embodiment of the invention is a method of fastening a device to one wall of a gastrointestinal organ comprising passing said device through a patient's abdominal skin, and through the patient's anterior stomach wall, wherein the device is in an undeployed configuration, passing an anchor through a patient's abdominal skin wherein the anchor is in an undeployed configuration, connecting the device and the anchor by means of a connector that passes through the wall of the gastrointestinal organ wherein the connector prevents the device and second anchor from moving apart, and deploying the anchor to its deployed configuration. In another embodiment, the device comprises an inflatable body attached to the connector, the body of the device having a deployed configuration when inflated that is relatively spherical and a reduced profile configuration when uninflated wherein it is readily deformable, wherein the connector is hollow and configured to allow inflation of the device by delivery of a filling substance through the connector to the device.

In another embodiment, the device is an electrical stimulator.

In yet another embodiment, the device is adapted to deliver a medicine.

In any of the embodiments, the reduced profile configuration can be substantially compressed and/or uninflated in the undeployed configuration, or inflated and/or uncompressed, in the deployed configuration.

In any of the embodiments, it can be the case that the gripping elements do not prevent movement of the second anchor along the longitudinal axis in either direction when the connector is disposed in the hole or other passageway when the second anchor is in its reduced profile configuration.

In any of the embodiments it may be the case that the gripper or gripping elements, when engaging a connector, allow movement of the connector in one direction relative to the anchor but prevents movement of the connector in an opposite direction relative to the anchor.

In any of the embodiments, the body of the first anchor can be inflatable, have a relatively planar deployed profile when inflated and a reduced profile configuration when uninflated, be readily deformable when uninflated, and the connector can be hollow and configured to allow inflation of the first anchor by delivery of a filling substance through the connector to the first anchor.

In any of the embodiments, the body of the second anchor can be inflatable, wherein the second anchor has a relatively planar deployed profile when inflated and a reduced profile configuration when uninflated, and wherein the second anchor is readily deformable when uninflated.

In any of the embodiments it may be the case that the anchor has an inflation tube connected to the body portion configured to allow inflation of the body portion by delivery of a filling substance through the inflation tube to the body portion.

In any of the embodiments, it can be the case that the filling substance hardens, cures, polymerizes, or become a gel over time, and is optionally bioabsorbable with further time.

In any of the embodiments, it can be the case that the second anchor has one or more attachment structures accessible from a top surface of the body.

In any of the embodiments, the first anchor, the second anchor, or both the first and the second anchors, can deliver an electrical signal to tissue when placed in contact with the tissue. In some embodiments, only the first or second anchor is placed which then delivers an electrical signal.

Another embodiment of the invention is a surgical instrument comprising a proximal end, a distal end, and a shaft with a channel, the distal end comprising a tissue penetrator adapted to penetrate, cut, or dilate the wall of a hollow organ, and a tissue grasper adapted to grasp a wall of a hollow organ, an expander within the channel of the surgical instrument wherein the expander can be deployed from within the channel of the instrument and extend through a wall of the hollow organ while the wall is being grasped by the tissue grasper, and is adapted to introduce a volume-filling material or device beyond the hollow organ.

Another embodiment of the invention is a surgical instrument comprising a proximal end, a distal end, and a channel, wherein the distal end comprises a tip which has an open configuration and a closed configuration, wherein in the closed configuration, the tip is adapted to penetrate a wall of a hollow organ, wherein in the open configuration, the tip can grasp the wall of the hollow organ, and wherein the channel comprises a diameter of about 2 mm to 12 mm.

Another embodiment of the invention is an anchor implantation instrument comprising, an outer sheath, a middle sleeve disposed within the outer sheath, an inner member disposed within the middle sleeve, and a channel within the inner member, wherein the middle sleeve has an outer diameter and a longitudinal axis, and the outer diameter of the middle sleeve is such that it can slide within the outer sheath along the longitudinal axis of the middle sleeve, wherein the inner member has an outer diameter, and the outer diameter of the inner member is such that it can slide within the middle sleeve along the longitudinal axis of the middle sleeve, wherein the inner member has a grasper suitable for grasping a foldable anchor and wherein the outer sheath has a distal portion which has an inner diameter sufficient to hold a foldable anchor in its folded configuration.

BRIEF DESCRIPTION OF THE DRAWING

FIGS. 2A and 2B are a perspective view and top view of one embodiment of an anterior anchor, respectively.

FIGS. 2C and 2D are side sectional views of the embodiment of the anterior anchor of FIGS. 2A and 2B, taken along the line B-B in FIG. 2B, in its deployed and reduced profile configuration, respectively.

FIGS. 2E and 2F are side sectional views of another embodiment of an anterior anchor, taken along the same line as FIGS. 2C and 2D, in its deployed and reduced profile configuration, respectively.

FIG. 5B is a perspective view of the distal end of the anchor implantation instrument of FIG. 5A and an anterior anchor and connector.

FIG. 5C is a side sectional view of the distal end of the anchor implantation instrument of FIGS. 5A and 5B, taken along line C-C in FIG. 5B, with the anterior anchor in its reduced profile configuration.

FIG. 7B illustrates the next step in one embodiment of a method of reducing the volume of the stomach. Shown is a side sectional view of a patient's abdomen with an anterior anchor in its deployed configuration on the connector, with the anterior and posterior walls of the stomach urged together.

FIG. 7C illustrates the next step in one embodiment of a method of reducing the volume of the stomach. Shown is a side sectional view of a patient's abdomen after the connector has been cut flush with the anterior anchor.

DETAILED DESCRIPTION OF THE PREFERRED EMBODIMENT

Anatomy of the Stomach

Figure 1A:
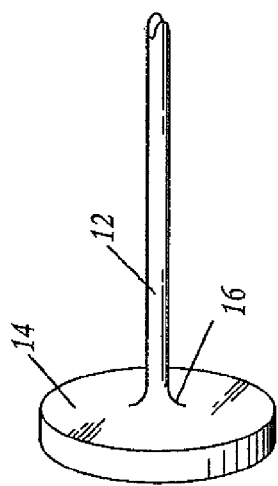
FIGS. 1A-1E are perspective views of embodiments of the posterior anchor and connector.

The region behind the stomach is referred to as the lesser peritoneal sac. It is a potential space between the retroperitoneum and the posterior wall of the stomach. To the left of the midline, the posterior wall of the stomach is generally free from the peritoneal surface of the retroperitoneum. To the right of the midline, the posterior wall of the stomach is more adherent to the retroperitoneum although the adherence is generally loose and the adhesions can be broken up rather easily with gentle dissection.

The stomach is comprised of several layers. The inner layer is the mucosa. The next layer is the submucosa followed by the outer muscular layers. Surrounding the muscular layers is the serosal layer. This layer is important with regard to implants and healing because it is the adhesive layer of the stomach; that is, it is the layer which, when breached, heals with scar tissue formation. Implants adhering to this layer are less likely to migrate into the stomach. Reference to "stomach wall" or "wall of the stomach" as used herein include the entire thickness of the stomach, including the mucosa, submucosa, muscular layers, and serosa. The "anterior wall of the stomach" is the portion of the stomach closest to the muscular abdominal wall and the "posterior wall of the stomach" is the part of the stomach closest to the retroperitoneum.

"Transgastric fastening assembly" refers to a permanent or semi-permanent implant and comprises at least one posterior anchor, at least one anterior anchor, and a fastener to connect the posterior and anterior anchors. The "fastener" can refer to any means of connection including but not limited to a material connection, an electromagnetic connection, or a chemical connection. As used herein, a "connector" is a fastener used to materially connect anterior and posterior anchors. As used herein, the "posterior anchor" is the anchor in a preferred embodiment which is adjacent to the posterior wall of the stomach when deployed. The "anterior anchor" is the anchor in a preferred embodiment which is approximated to the anterior wall of the stomach when deployed.

As used herein when referring to portions of a surgical instrument, "proximal" refers to the end of the instrument which is closest to the surgeon when the instrument is used for its intended purpose, and "distal" refers to the end of the instrument which is closest to the patient when the instrument is used for its intended purpose. When used to refer to the gastrointestinal tract, "proximal" is toward the mouth and "distal" is toward the anus.

Percutaneous surgery typically means that the procedure is performed under visualization (e.g. fluoroscopic, MRI, CAT Scan, Ultrasound, Endoscopic) which is not direct visualization and which requires an incision, typically small, somewhere in the skin. More recently, the boundaries of percutaneous surgery have been blurred as some procedures involve both direct visualization, such as with a laparoscope, and percutaneous methodology. An example of such a procedure is the laparoscopic placement of a jejunostomy or gastric feeding tube. Laparoscopic methods require general anesthesia to paralyze the abdominal muscles so that the abdomen can be filled with gas. Consequently, general anesthesia is required so as to enable paralysis of the diaphragm and respiratory muscles.

As used herein, "percutaneous" refers to a procedure wherein general anesthesia and general pneumoperitoneum are not used or the procedure utilizes incisions through the skin of the abdomen for access to the surgical site and not for visualization. Therefore, as used herein, percutaneous surgery and laparoscopic surgery are mutually exclusive. In the preferred embodiment, the methods described herein are performed percutaneously, although laparoscopic methods are contemplated.

Structures

Transgastric Fastening Assembly

Figure 1C:
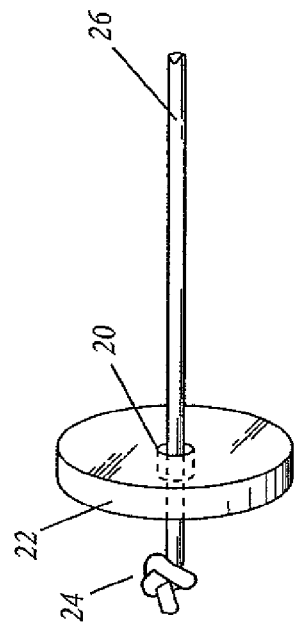
Figure 1E:
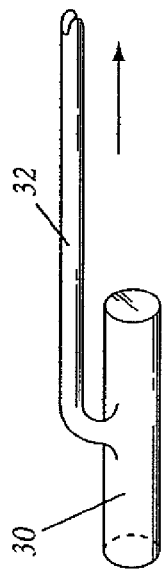
Figure 1B:
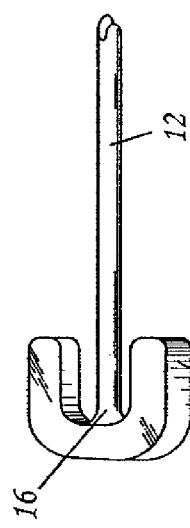

Referring to FIGS. 1A and 1B, one embodiment of the posterior anchor 14 and connector 12 are shown in a deployed configuration (FIG. 1A), and reduced profile configuration (FIG. 1B). The connector 12 is preferably made of a biocompatible semi-rigid polymer, but it can be made from various kinds of suitable biocompatible materials known to those of skill in the art including metals, such as titanium and platinum, metal alloys, such as stainless steel, nickel-titanium, and cobalt-chromium, man-made polymers, such as polyurethane, silicone elastomers, polyglycolic acid, polylactic acid, poly (c-caprolactone), polyvinylidene fluoride (PVDF), PTFE, polypropylene, or natural fibers such as silk. These materials can be used singly or in combination. For example, one portion of the connector may be bioabsorbable and another portion of the connector may be permanent. The connector 12 can vary in thickness, shape, and rigidity. For example, in the embodiment shown in FIG. 1A, the connector 12 is substantially rod-shaped, with a circular cross-section, and is semi-rigid. Those of skill in the art will recognize that the cross-section of the connector can be any of a number of shapes, such as square, hexagonal, oval, etc. In other embodiments, the connector 12 is thin and flexible, such as a surgical suture, and in still others it is rigid.

In a preferred embodiment, the posterior anchor 14 is made from a biocompatible, radio-opaque or magneto-opaque semi-rigid polymer; it can also be made from various kinds of suitable materials known to those of skill in the art including metals, metal alloys, plastics, natural materials or combinations thereof as discussed above. The posterior anchor 14 can be solid, or alternatively, can be porous, mesh-like, lattice-like, or umbrella-like. In a preferred embodiment, the posterior anchor is porous or has a porous mesh attached to it to encourage fibrous ingrowth such that it becomes permanently attached to the stomach or intestinal wall. Coatings can be added to the anchor to encourage tissue ingrowth. In other embodiments, the posterior anchor is solid and treated to discourage tissue ingrowth. In other embodiments, the anterior anchor has a xenograft or allograft material attached to the anchor. In a preferred embodiment, the posterior anchor 14 is disc-shaped, but those of skill in the art will recognize that other embodiments are possible, such as those shown in FIGS. 1C and 1D, or disclosed in U.S. Patent Application Publication No. 2004/0122456 which is herein incorporated by reference; note particularly the description of anchor structures. The posterior anchor can also be bioabsorbable in whole or in part in some embodiments.

In the embodiment shown in FIGS. 1A and 1B, the connector 12 is fastened to the posterior anchor 14 at an attachment point 16 which is preferably a permanent, e.g. welded or molded, connection. Such a weld or connection can comprise, for example, a thermoformed polymer, a metallic weld, or a molded or other integral structure. In a preferred embodiment, a biocompatible thermoformed polymer is used because of its flexibility and ability to yield to the continuous motion of the stomach. More preferably, the connector and posterior anchor are produced as a single, continuous injection molded component.

Other suitable means of fastening the connector to the posterior anchor are also contemplated and do not necessarily result in a connector and posterior anchor becoming permanently attached. For example, in one embodiment shown in FIG. 1C, one end of the connector is passed through a hole 20 near the center of the posterior anchor 22, and a stop 24, such as a knot or enlarged molded region, is formed on the end of the connector to prevent its passage back through the hole in the posterior anchor. In this embodiment, the posterior anchor 22 can be free to move along the length of the connector 26, but is prevented from being removed from one end of the connector by the stop 24.

In the embodiment shown in FIGS. 1A and 1B, the posterior anchor 14 preferably has a deployed configuration (FIG. 1A), and reduced profile configuration (FIG. 1B). The posterior anchor 14 can be deformed to a folded configuration wherein its profile is reduced to facilitate insertion of the anchor through the walls of the stomach or other tissue as described in more detail below, In one embodiment, the posterior anchor 14 is made of a semi-flexible material having shape memory, so that once the anchor is deployed within the patient, it will return to its original shape shown in FIG. 1A, preventing it from being easily pulled back through the tissue. Preferably, the posterior anchor is inflatable in place oft or in addition to, having shape memory, which allows for a much larger deployed profile relative to its undeployed profile. (See below).

Figure 1D:
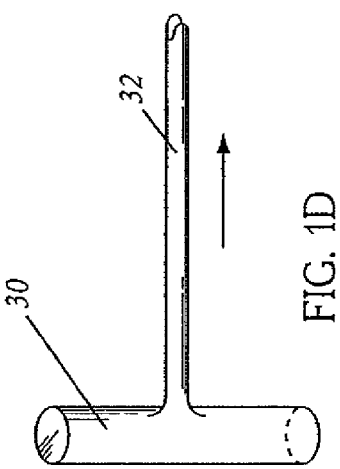

FIGS. 1D and 1E show an alternative embodiment of the posterior anchor 30 and connector 32 in a deployed configuration (FIG. 1D), and a reduced profile configuration (FIG. 1E). In this embodiment, the posterior anchor 30 is elongated, having major and minor dimensions, and preferably having a rod or bar shape. By aligning the connector 32 substantially parallel to the posterior anchor 30, its profile is reduced to facilitate insertion of the anchor through the walls of the stomach or other tissue. When the anchor leaves its surrounding sheath (see below), tension on the connector 32 in the direction of the arrow in FIG. 1E will urge the posterior anchor 30 into a substantially perpendicular orientation relative to the connector 32, as shown in FIG. 1D, preventing it from easily being pulled back through the tissue. The connection between the posterior anchor 30 and the connector 32 can be hinged. Alternatively, the connector 32 can be made of a semi-rigid material which is permanently connected or welded to the posterior anchor 30. If the connector is deformed to a bent position, shown in FIG. 1E, it will return to its original straight shape shown in FIG. 1D once the anchor is deployed within the patient, preventing the posterior anchor from easily being pulled back through the tissue. This anchor 30 can be inflatable as well, which allows for a much larger deployed profile relative to its undeployed profile.

Figure 1G:
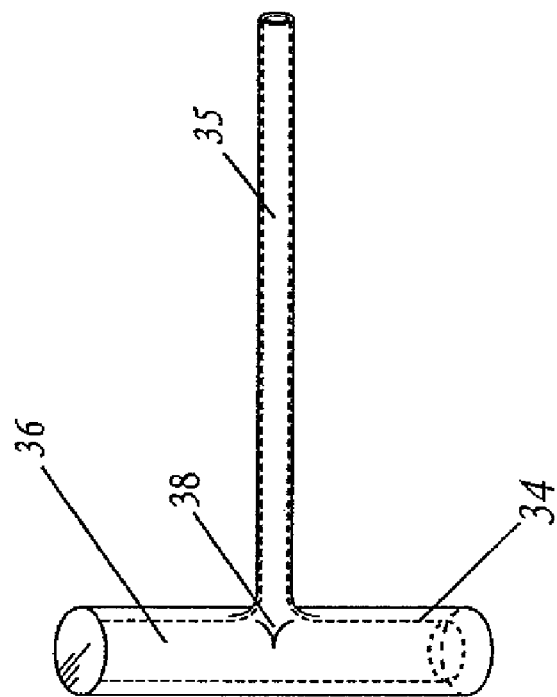
FIGS. 1F and 1G are side views of an inflatable embodiment of posterior anchor and connector.
Figure 1F:
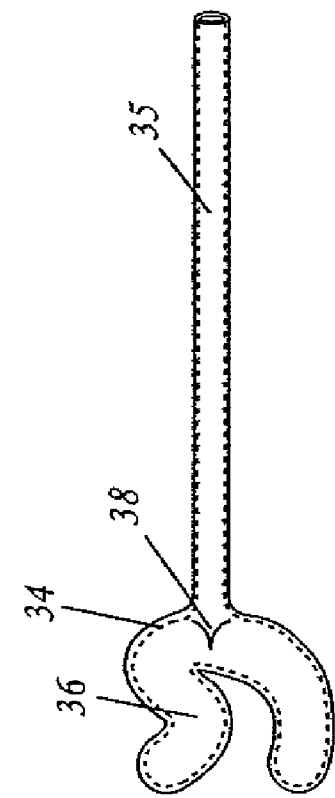

In a preferred embodiment, shown in FIGS. 1F and 1G, the posterior anchor is inflatable. The anchor has an inflatable disc-shaped body 34 which is readily deformable when in its reduced profile (i.e., uninflated) configuration as shown in FIG. 1F. In the preferred embodiment, the posterior anchor body 34 is disc-shaped, but those of skill in the art will recognize that other embodiments are possible, such as those shown in FIGS. 1C and 1D, or in which the inflatable anchors are square shaped, rectangular, or amorphous, or have a shape disclosed in U.S. Patent Application Publication No. 2004/0122456 which is herein incorporated by reference; note particularly the description of anchor structures. The body can be inflated with a substance delivered through a hollow connector 35. When the interior space 36 of the anchor body is inflated, the anchor assumes its deployed configuration shown in FIG. 1G.

The inflatable posterior anchor can have a valve 38 located between the anchor body 34 and the connector 35. Alternatively, the valve is located in the portion of the connector located outside the patient, the valve (e.g. stopcock type valve) being controlled by the operator until the anterior anchor is placed (see below). In this alternative embodiment, the filling substance is trapped in the posterior anchor after the anterior anchor is deployed and the connector is cut and sealed, preferably flush with the anterior anchor (see below). The filling substance can be a gas, liquid, or material which changes phase with time (i.e. it may harden, cure, polymerize, or become a gel with time). Preferably, the surface of the posterior anchor adjacent to the posterior-wall of the stomach has a mesh fixed to it to encourage tissue ingrowth. In some embodiments, part, or all of the anchor material is comprised of a biodegradeable material.

Figure 2A:
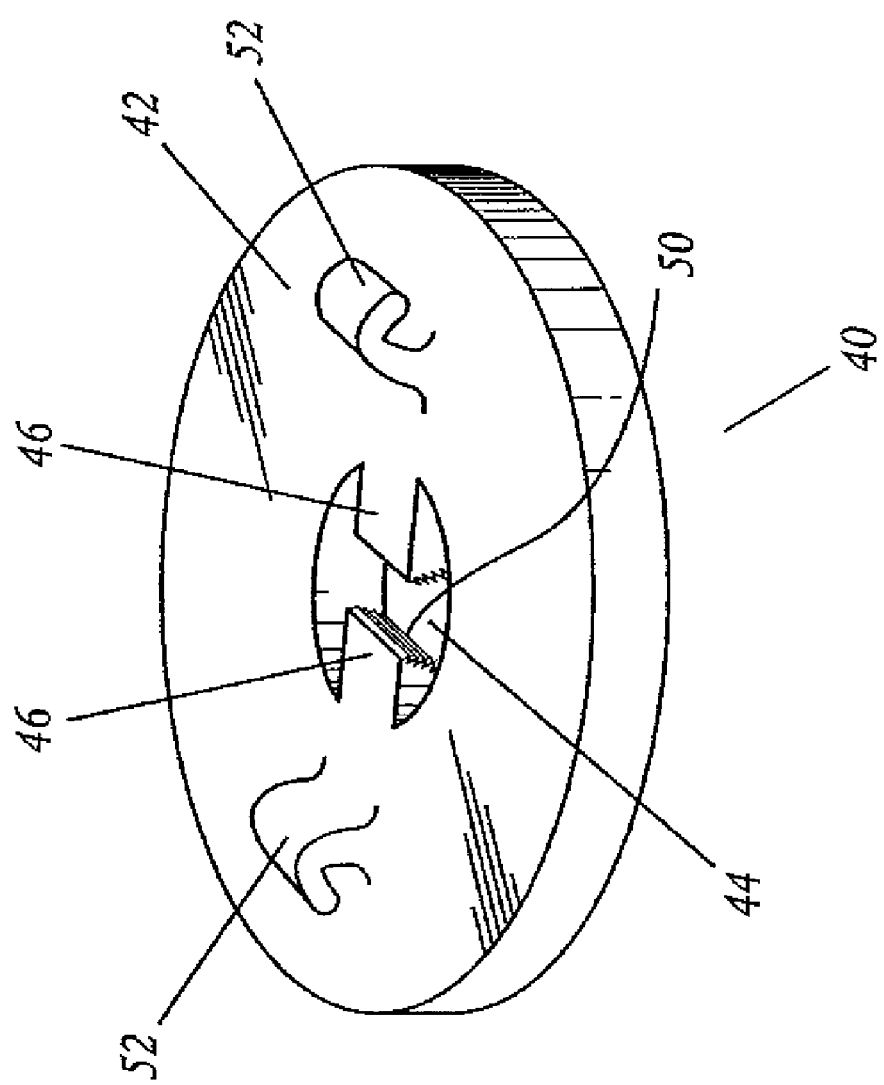

FIGS. 2A (perspective view) and 2B (plan view) show an embodiment of the anterior anchor 40. The anterior anchor has a disc-shaped body 42 with a hole or other passageway 44 substantially in the middle of the body. Two gripping elements 46 project into the center of the hole or other passageway. With respect to the gripping elements, there can be as few as one or more than two. The gripping elements may have teeth 50 angled toward the top surface of the anchor. Optionally, two hooks 52, or other graspable recesses, appendages, or structures, are located on the top surface of the anterior anchor. Hooks 52 allow for attachment of a surgical instrument during deployment of the anterior anchor in the patient as described below. Alternatively, there can be none, one, or more than two graspable recesses, appendages, or structures on the top surface of the anchor. In the preferred embodiment, the anterior anchor body 42 is disc-shaped, but those of skill in the art will recognize that other embodiments are possible, as disclosed in U.S. Patent Application Publication No. 2004/0122456 which is herein incorporated by reference; note particularly the description of anchor structures.

FIGS. 2C and 2D are cross sections of the anterior anchor of FIGS. 2A and 2B, taken along the line B-B in FIG. 2B. FIG. 2C shows the anterior anchor in its deployed configuration with the connector 12 of FIG. 1A passing through the hole or other passageway 44 in the body of the anchor. In the deployed configuration, the gripping elements 46 and teeth 50 engage the connector 12 with sufficient pressure to prevent movement of the anchor along the connector 12 in the direction of the arrow in FIG. 2C, which would increase the distance between the anterior anchor and posterior anchor (not shown). In FIG. 2D, the anterior anchor 40 is in its reduced profile configuration with the connector 12 of FIG. 1A passing through the hole or other passageway 44 in the body of the anchor. Preferably, the anterior anchor is made of a semi-rigid polymer which allows the anchor to be deformed into a substantially folded configuration illustrated in FIG. 2D. When in this configuration, the gripping elements 46 and teeth 50 do not significantly engage the connector 12. This allows movement of the anterior anchor 40 along the length of the connector 12 in the directions illustrated by the arrows in FIG. 2D. Once the anterior anchor is in the desired position along the connector 12, the anterior anchor is permitted to return to the configuration shown in FIG. 2C, and the gripping elements 46 and teeth 50 engage the connector 12, thus preventing movement between the connector 12 and the anterior anchor 40.

In an alternative embodiment, it is contemplated that the connector 12 can have notches 51, which interact with gripping elements 46 in a ratchet-and-pawl mechanism similar to that used in cable ties, providing a one-way adjustability, in which the posterior and anterior anchors can be moved toward each other, but not away from each other.

FIGS. 2E and 2F illustrate another embodiment of an anterior anchor 60 which is similar to the one illustrated in FIGS. 2C and 2D. In FIG. 2E, the gripping elements 62 and teeth 64 are oriented so that the anterior anchor can be deformed such that the top surface of the anchor is folded inward as illustrated in FIG. 2F. This is in contrast to the embodiment illustrated in FIG. 2D where the bottom surface of the anchor is folded inward. The teeth 64 in FIG. 2E are angled toward the top surface of the anterior anchor and engage the connector 12 of FIG. 1A such that they prevent movement of the anterior anchor along the connector 12 in the direction of the arrow in FIG. 2E, which would increase the distance between the anterior anchor and posterior anchor (not shown).

Figure 2G:
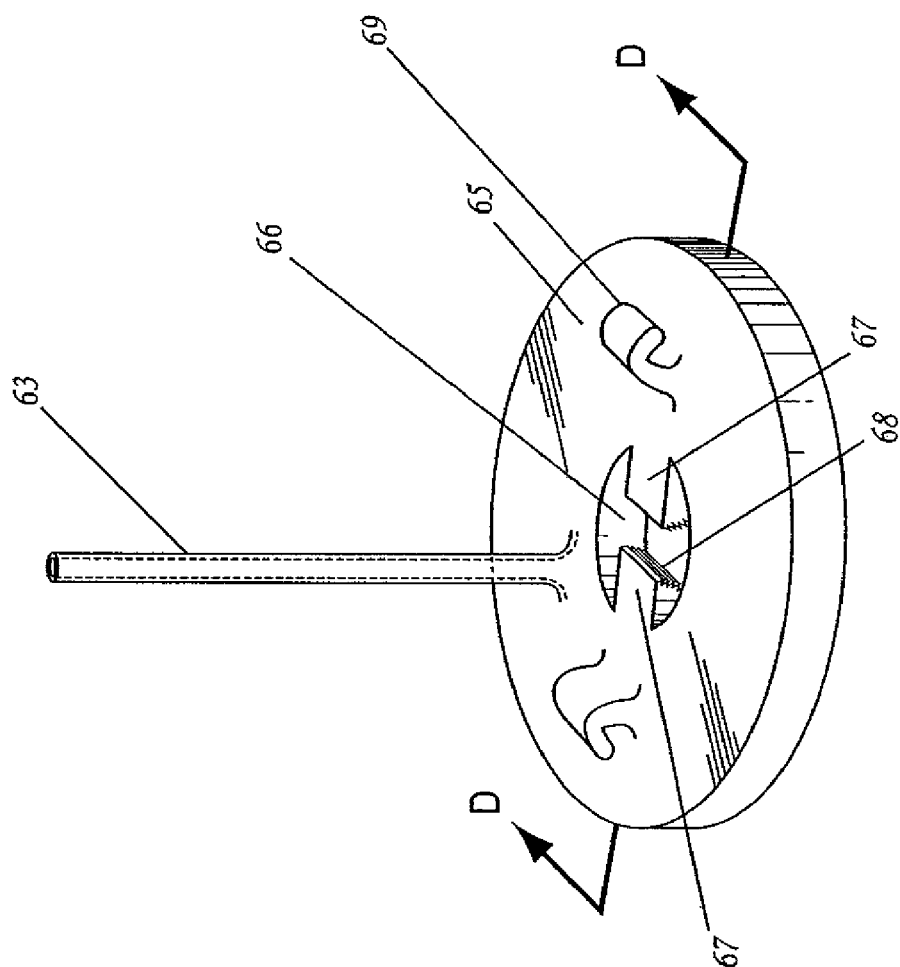
FIG. 2G is a perspective view of an inflatable embodiment of an anterior anchor.

FIG. 2G is a perspective view of a preferred embodiment where the anterior anchor is inflatable. The anterior anchor has a hollow, inflatable disc-shaped body 65 with a hole or other passageway 66 substantially in the middle of the body. Two gripping elements 67 project into the center of the hole or other passageway, although there can be as few as one or more than two. The gripping elements can have teeth 68 angled toward the top surface of the anchor. Alternatively, in a preferred embodiment, the gripping elements are in the form of a rough surface rather than the protruding elements as shown in FIG. 2G. Such a surface, which may be a sandpaper-like surface, creates enough friction to prevent movement in either direction along the connector. Optionally, two hooks 69 are located on the top surface of the anterior anchor. Hooks 69 facilitate grasping by a surgical instrument during deployment of the anterior anchor in the patient as described below. Alternatively, rather than hooks, there can be one or more graspable protrusions on the body. In yet another embodiment, there are no hooks or graspable protrusions, and the body of the anchor is grasped directly to manipulate the anchor. In another embodiment, protrusions 69 are magnetic or otherwise sticky in nature to facilitate attachment to a surgical instrument.

An inflation tube 63 is used to inflate and deflate the anchor. This inflation tube may or may not have a valve. In one preferred embodiment, the anterior anchor is filled with gas or fluid through the inflation tube and the fluid is held inside the anchor through an external (e.g. stopcock) valve controlled by the operator. When the inflation tube is cut at the end of the procedure, the inflation line is crimped closed thereby locking the inflating substance inside the anchor. Alternatively, the shears used to cut the inflation line can be metal and an electrocautery current can be applied through the shears and to the inflation line to weld it closed.

Figure 2H:
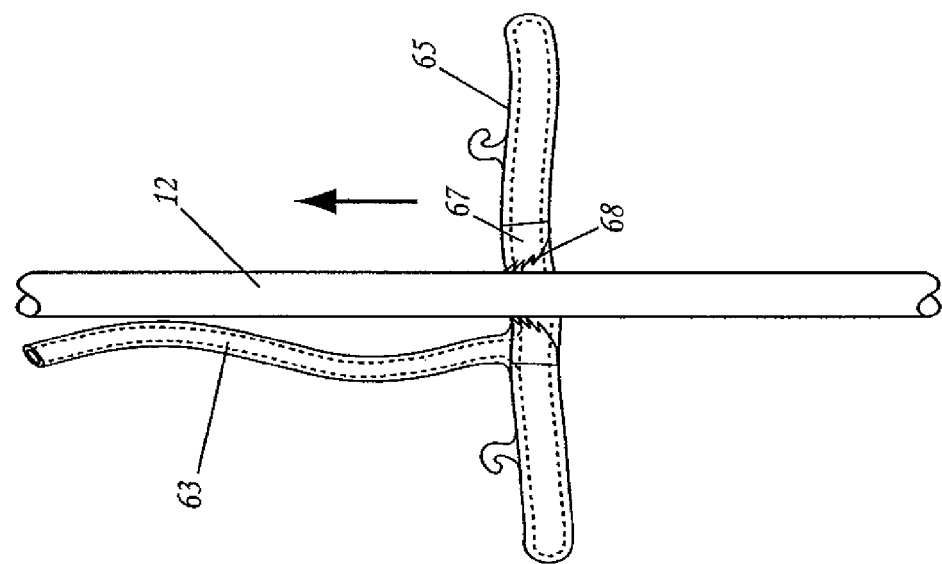
FIGS. 2H and 2I are side sectional views of the embodiment of the anterior anchor of FIG. 2G, taken along the line D-D in FIG. 2G, in its deployed and reduced profile configuration, respectively.
Figure 2I:
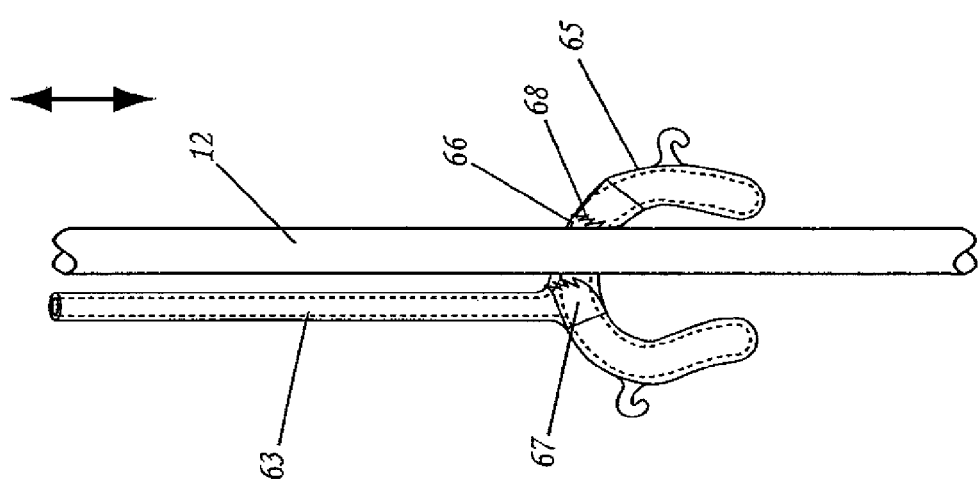

FIGS. 2H and 2I are cross sections of the anterior anchor of FIG. 2G, taken along the line D-D in FIG. 2G. The disc-shaped body 65 is readily deformable when in its reduced profile (i.e., uninflated) configuration as shown in FIG. 2I. The body can be inflated with a substance delivered through the inflation tube 63. When anchor body is inflated, the anchor assumes its deployed (i.e. inflated) configuration as shown in FIG. 2H with the connector 12 of FIG. 1A passing through the hole 66 in the body of the anchor. In the deployed configuration, the gripping elements 67 and teeth 68 engage the connector 12 with sufficient pressure to prevent movement of the anchor along the connector 12 in the direction of the arrow in FIG. 2H, which would increase the distance between the anterior anchor and posterior anchor (not shown). Alternatively, rather than defined gripping elements and teeth, the surface of body which defines the sides of the hole or other passageway 66 can be configured such that when the anchor body is inflated, the sides of the hole or other passageway expand to substantially close off the hole or other passageway and limit movement of the anchor relative to the connector through friction between the connector and the anchor.

In FIG. 2I, the anterior anchor 65 is in its reduced profile (i.e. uninflated) configuration with the connector 12 of FIG. 1A passing through the hole 66 in the body of the anchor. When in this configuration, the anchor body is readily deformable and the gripping elements 67 and teeth 68 do not significantly engage the connector 12. This allows movement of the anterior anchor 65 along the length of the connector 12 in the directions illustrated by the arrows in FIG. 2I. Once the anterior anchor is in the desired position along the connector 12, the anterior anchor is inflated by a filling substance delivered through the inflation tube 63, and the anchor assumes its deployed (i.e. inflated) configuration as shown in FIG. 2H; the gripping elements 67 and teeth 68 engage the connector 12, thus restricting movement of the anterior anchor 65 in one or both directions along the length of the connector 12. The filling substance can be a gas, liquid, or material which changes phase with time (i.e. it may harden, cure, polymerize, or become a gel with time).

Figure 3C:
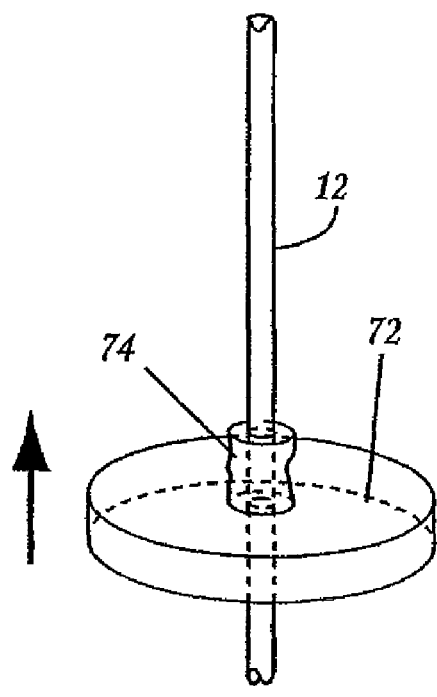
FIGS. 3B and 3C are perspective views of the embodiment of the anterior anchor shown in FIG. 3A in its reduced profile and deployed configuration, respectively.
Figure 3D:
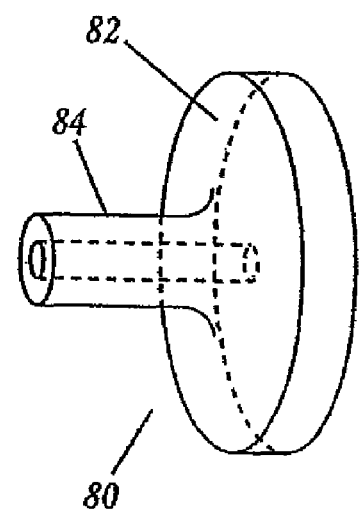
FIG. 3D is a perspective view of another embodiment of an anterior anchor.
Figure 3B:
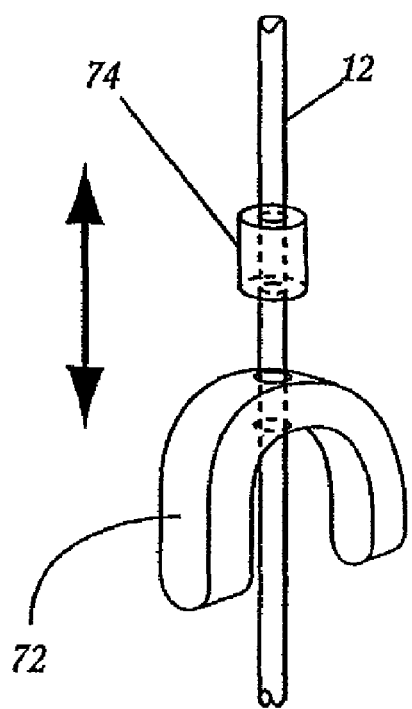
Figure 3A:
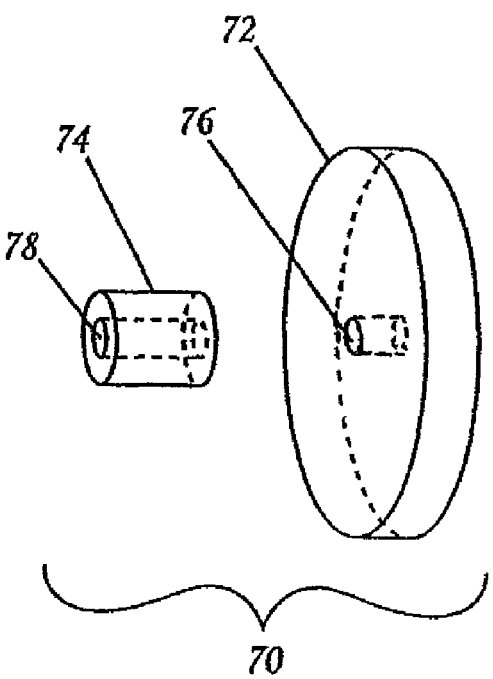
FIG. 3A is a perspective view of another embodiment of an anterior anchor.

FIG. 3A illustrates another embodiment of an anterior anchor 70 consisting of two parts, an anchor body 72 and a readily deformable collar 74. The anchor body and collar have a central hole or other passageway (76 and 78 respectively) through which the connector can pass. Preferably, the anterior anchor body is made of a semi-rigid polymer which can be deformed into a folded configuration with a reduced profile as illustrated in FIG. 3B. Preferably, the readily deformable collar 74 is permanently deformable; i.e., once deformed, it does not return to its original shape. As illustrated by the arrow in FIG. 3B, both the collar 74 and anchor body 72 can move along the connector 12 of FIG. 1A. Once the anchor body 72 is in the desired position, the collar 74 is crushed, such that the collar 74 engages the connector 12 and can no longer move along the length of the connector 12. This prevents the anchor body 72 from moving along the length of the connector 12 in the direction of the arrow illustrated in FIG. 3C, which would increase the distance between the anterior anchor and posterior anchor (not shown). FIG. 3D illustrates an alternative embodiment of the anterior anchor 80, where the anchor body 82 and deformable collar 84 are a single piece.

In a preferred embodiment, the anterior anchor is made from a biocompatible, radio- or magneto-opaque polymer, but it can be made from various kinds of suitable materials known to those of skill in the art including metals, metal alloys, plastics, natural materials or combinations thereof as disclosed above. The anterior anchor can be solid, or alternatively, can be porous, mesh-like, umbrella-like or lattice-like. In a preferred embodiment, the anterior anchor is porous, mesh-like, umbrella-like or lattice-like to encourage fibrous ingrowth such that it becomes permanently attached to the stomach wall. Coatings can be added to the anchor, or a mesh material such as polypropylene can be fixed to the anchor surface, such that it touches the anterior stomach wall and encourages tissue ingrowth. In other embodiments, the anterior anchor is solid and treated to discourage tissue ingrowth. In other embodiments, the anterior anchor has a xenograft or allograft material attached to the anchor. In a preferred embodiment, the anterior anchor is disc-shaped and substantially flat, but those of skill in the art will recognize that other embodiments are possible.

Surgical Instruments

Figure 4A:
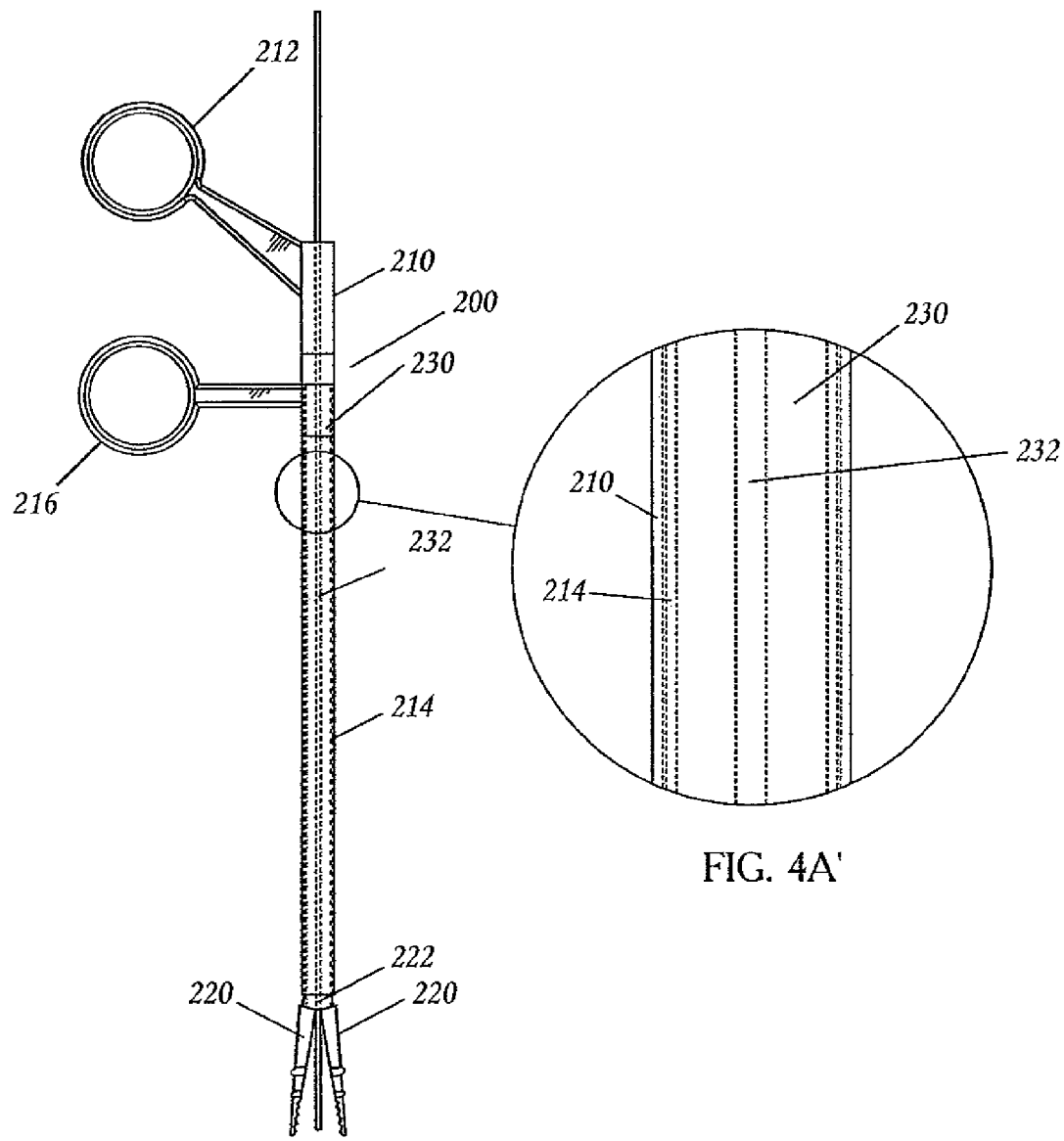
FIGS. 4A and 4A' are a side and blow-up view, respectively, of one embodiment of a tissue grasping instrument with the distal end in its open configuration.
Figure 4B:
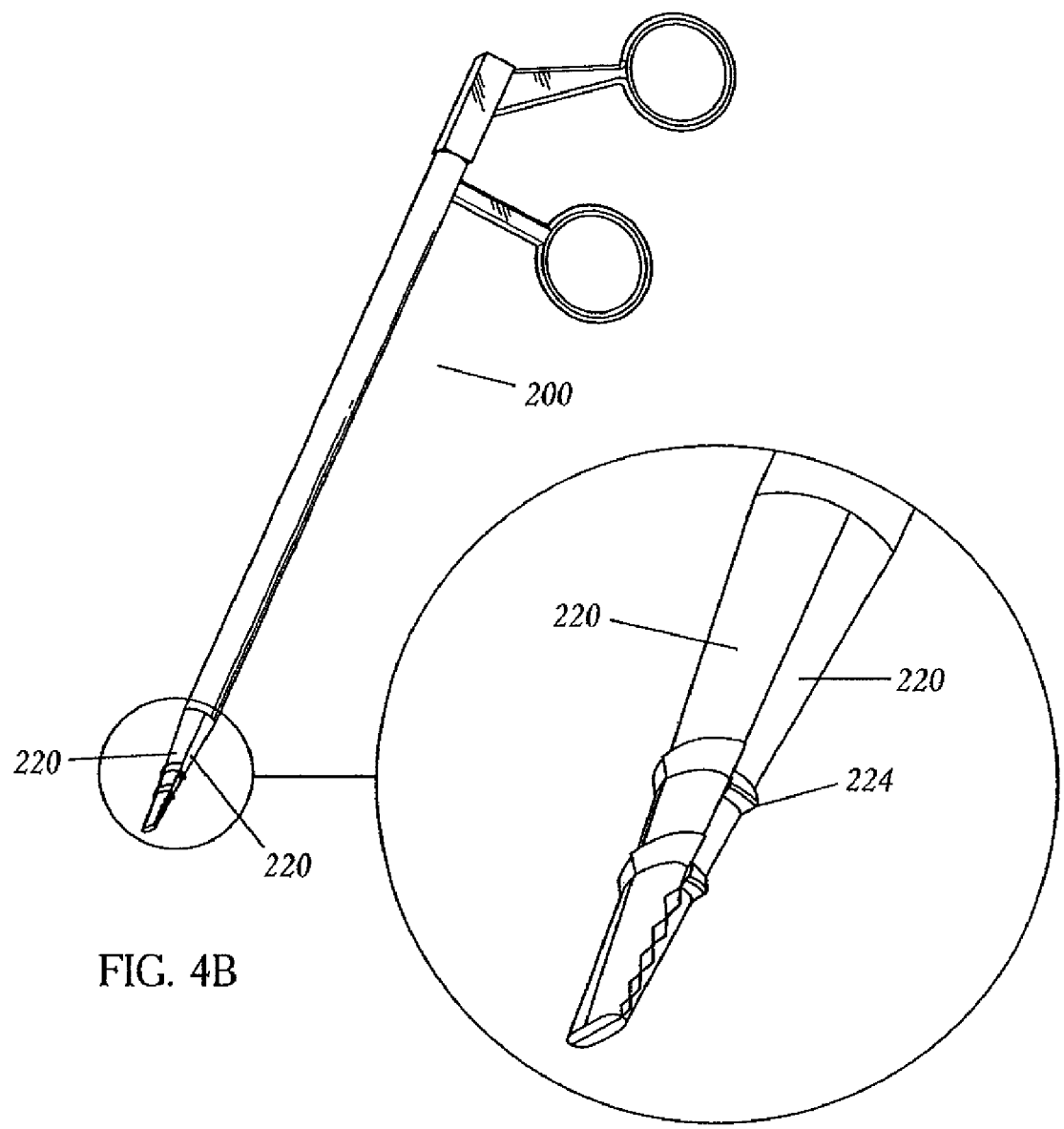
FIGS. 4B and 4B' are a perspective and blow-up view, respectively, of the tissue grasping instrument of FIG. 4A with the distal end in its closed configuration.

FIG. 4A illustrates one embodiment of a tissue grasping instrument 200. The tissue grasper has a tubular outer sleeve 210 to which a portion of a handle 212 is attached at the proximal end. As shown in more detail in the blow-up, FIG. 4A', disposed within the outer sleeve 210 is a tubular inner member 214 which has an outer diameter such that it can slide within the outer sleeve 210 in the longitudinal axis of the outer sleeve 210 but cannot move substantially transverse to the longitudinal axis of the outer sleeve 210. At the proximal end of the inner member, a second portion of a handle 216 is attached. At the distal end of the inner member is a pair of jaws 220 which is connected to the inner member at a hinge point 222. When the distal end of the inner member 214 is displaced from the inside of the outer sleeve 210 such that the hinge point 222 is outside the outer sleeve, the jaws 220 assume their open position as depicted in FIG. 4A. As the hinge point 222 is withdrawn into the outer sleeve 210, the outer sleeve forces the jaws 220 into their closed position, as illustrated in FIG. 4B. The opening and closing of the jaws 220 can be accomplished by manipulation of the handle portions 212 and 216.

Figure 4C:
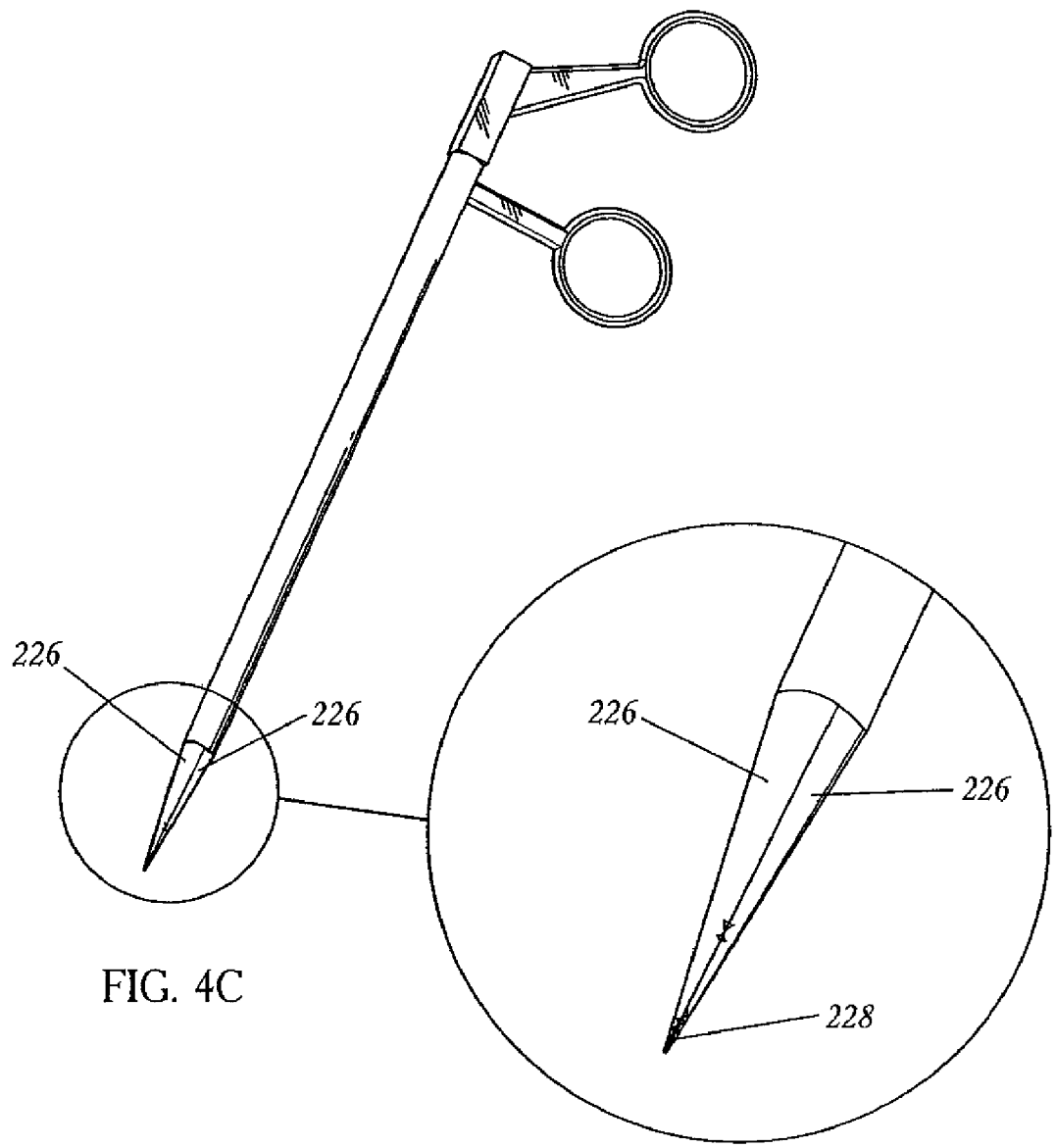
FIGS. 4C and 4C' are a perspective and blow-up view, respectively, of another embodiment of the tissue grasping instrument with the distal end in its closed configuration.

The distal end of the grasping instrument 200 is configured to cut, puncture, or dilate tissue when the jaws 220 are in the closed position. In one embodiment shown in FIG. 4B, the jaws 220 have screw-thread-shaped protrusions 224 on the surface. By rotating the instrument as it passes through tissue, the protrusions 224 facilitate the penetration of tissue, similar to a corkscrew. In another embodiment illustrated in FIG. 4C, the instrument has jaws 226 that form a sharp tip 228 when closed. In yet another embodiment, the jaws form a blade which can cut through tissues when in the closed position. One of skill in the art would recognize that the above configurations can be combined, or that other configurations are possible which facilitate the passage of the tip of the instrument through the wall of the stomach or other tissue.

It also should be realized to one skilled in the art that the closed end of the grasping device does not have to be the only instrument responsible for cutting through the tissue; the central lumen 230 of the device can be utilized to assist in tissue penetration. For example, a needle (e.g. a Verres needle) 232 can be passed through the lumen and the needle 232 can make the initial puncture through the tissue. The configuration of the distal end of the grasper is meant to be a tissue, dilator and facilitator of the entry into the stomach after the needle makes the initial puncture. For safety, the needle can be retracted as the tissue grasper dilates the tissue.

In the embodiment of the tissue grasper 200 illustrated in FIG. 4A, the inner member 214 and outer sleeve 210 have a central tunnel 230 that extends the length of the tissue grasper. The tunnel 230 allows for the passage of an expanding means such as a needle 232, or other instrument or device such as the posterior or anterior anchor described above, through the length of the tissue grasper as shown in FIG. 4A. The central tunnel is also adapted such that a radially dilating sheath can be inserted through it. The diameter of the central lumen is preferably at least 4 mm, but can be at least 5, 6, 7, 8, 9, 10, 11, or 12 mm. In an alternative embodiment, the distal jaws can be configured to close through an electromechanical means or purely magnetic means such that the inner member is not necessary.

Figure 5A:
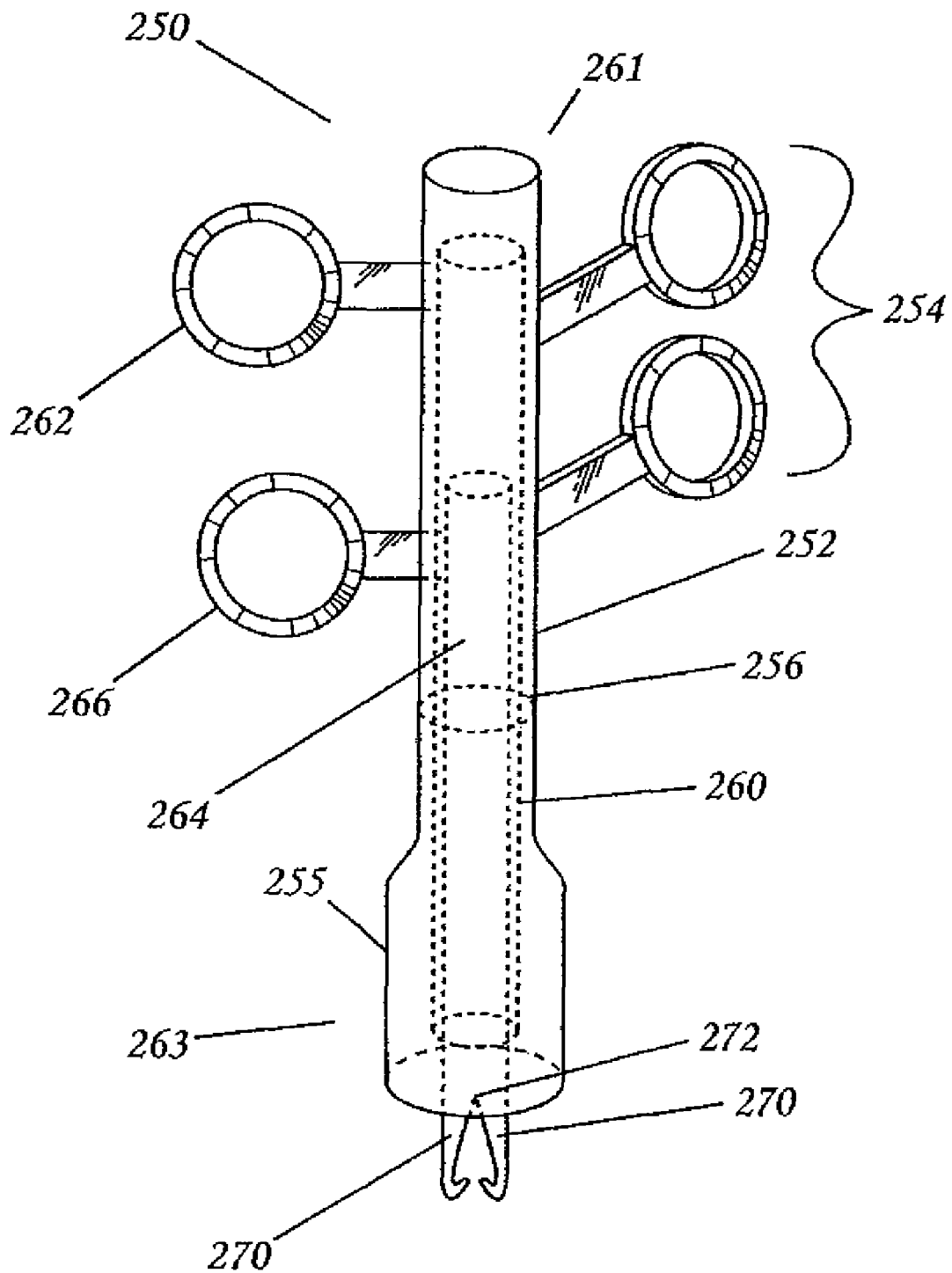
FIG. 5A is a side view of one embodiment of an anchor implantation instrument.

FIG. 5A illustrates one embodiment of an anchor implantation instrument 250. The implantation instrument has a tubular outer sheath 252 which has a handle 254 attached. At the distal end, the outer sheath flairs out to an increased diameter 255 to accommodate the anterior anchor in its substantially folded position as illustrated in FIG. 5C. Within the outer sheath is an anchor grasping instrument 256 similar to the tissue grasping instrument of FIG. 4A, made up of a tubular middle sleeve 260 and a tubular inner member 264. The tubular middle sleeve 260 has an outer diameter such that it can slide within the outer sheath 252 in the longitudinal axis of the outer sheath 252 but cannot move substantially transverse to the longitudinal axis of the outer sheath 252.

The tubular middle sleeve 260 of the anchor grasping instrument has a portion of a handle 262 attached at the proximal end 261 of the instrument. Disposed within the middle sleeve 260 is a tubular inner member 264 which has an outer diameter such that it can slide within the middle sleeve 260 in the direction of the longitudinal axis of the middle sleeve 260 but cannot move substantially in transverse to the longitudinal axis of the middle sleeve 260. At the proximal end of the inner member, a second portion of a handle 266 is attached.

The distal tip 263 of the instrument is illustrated in more detail in FIGS. 5B and 5C, with the inclusion of the anterior anchor 40 of FIG. 2A and connector 12 of FIG. 1A. FIG. 5C is a side section view taken along the line C-C of FIG. 5B. At the distal end 263 of the inner member 264 is a pair of hooking members 270 which are connected to the inner member at a hinge point 272. When the distal end of the inner member 264 is displaced from the inside of the middle sleeve 260 such that the hinge point 272 is outside the middle sleeve, the hooking members 270 assume their open position as depicted in FIG. 5B. As the hinge point 272 is withdrawn into the middle sleeve 260, the middle sleeve forces the hooking members 270 into a closed position, as illustrated in FIG. 5C. The opening and closing of the hooking members 270 can be accomplished by manipulation of the handle portions 262 and 266.

The instrument is designed such that the anterior anchor is easily manipulated. When the anterior anchor is in its substantially folded or compressed configuration as in FIG. 5C, the entire anterior fastener assembly can be manipulated along the longitudinal axis of the connector 12. FIG. 5C depicts the assembly as it would be introduced over the connector 12 and into the patient. The operator pulls the connector 12 toward the operator such that the posterior anchor is urged toward the anterior anchor. When in position, the operator deploys anterior anchor 40. To deploy anterior anchor 40, outer sheath 252 is pulled back toward the operator. Middle sleeve 260 is then withdrawn proximally toward the operator as well. Hooking members 270 tend to fan out as the middle sleeve is pulled back and will release hooks 52. Once deployed, anterior fastener 40 is now fixed in a longitudinal position along the connector 12.

If the surgeon wants to readjust the anterior anchor, connector 12 is manipulated so that the hooks 52 of the anterior anchor are brought into contact with hooking members 270; middle sleeve 260 is advanced distally from the operator, permitting hooking members 270 to engage the hooks 52; such contact is facilitated by pulling back (proximally) on the connector 12. By manipulating the middle sleeve 260 over the hooking members 270, the hooks 274 on the ends of the hooking members 270 can engage the hooks 52 on the anterior anchor 40. The outer sheath 252 is then slid over the anterior anchor 40 (or the anchor-middle sleeve complex is withdrawn into the outer sheath 252), until it is compressed into an undeployed configuration as shown in FIG. 5C. As described above, when the anterior anchor 40 is in a substantially compressed configuration, it can move along the length of the connector 12 in either direction.

In an embodiment where an inflatable anterior anchor such as the one illustrated in FIGS. 2G-2I is utilized, a standard laparoscopic grasping instrument (with teeth) can be used to manipulate the anterior anchor. When the inflatable anterior anchor is in the uninflated position, it is sufficiently compliant such that it can easily be passed through a laparoscopic port prior to inflation and deployment or after it has been deflated for readjustment; the middle sheath may not be necessary because the compliance of the balloon enables easy compression into the outer sheath. The inflation tube 63 passes through the laparoscopic port and out of the patient. This allows the inflation tube 63 of the anchor to be temporarily opened or closed outside the patient allowing for deflation and reinflation until the anchor is in place. The inflation tube is then sealed and cut off, preferably substantially flush to the surface of the anterior anchor.

Methods

Implantation of the Transgastric Fastening Assembly

Figure 6B:
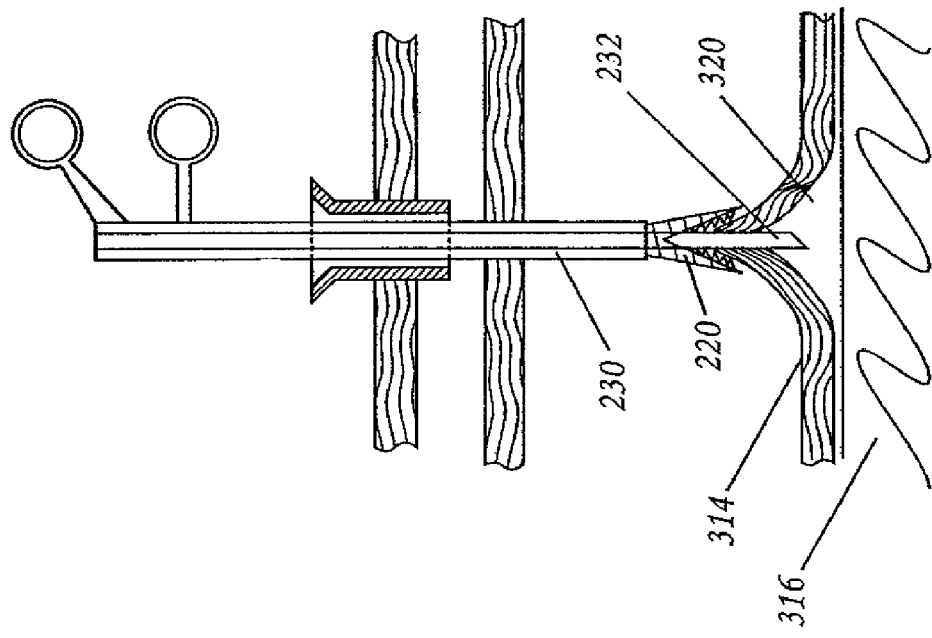
FIG. 6B illustrates the next step in one embodiment of a method of reducing the volume of the stomach. Shown is a side sectional view of a patient's abdomen with the instrument of FIG. 4 grasping the posterior wall of the stomach and a needle being inserted into the potential space of the lesser peritoneal sac.
Figure 6A:
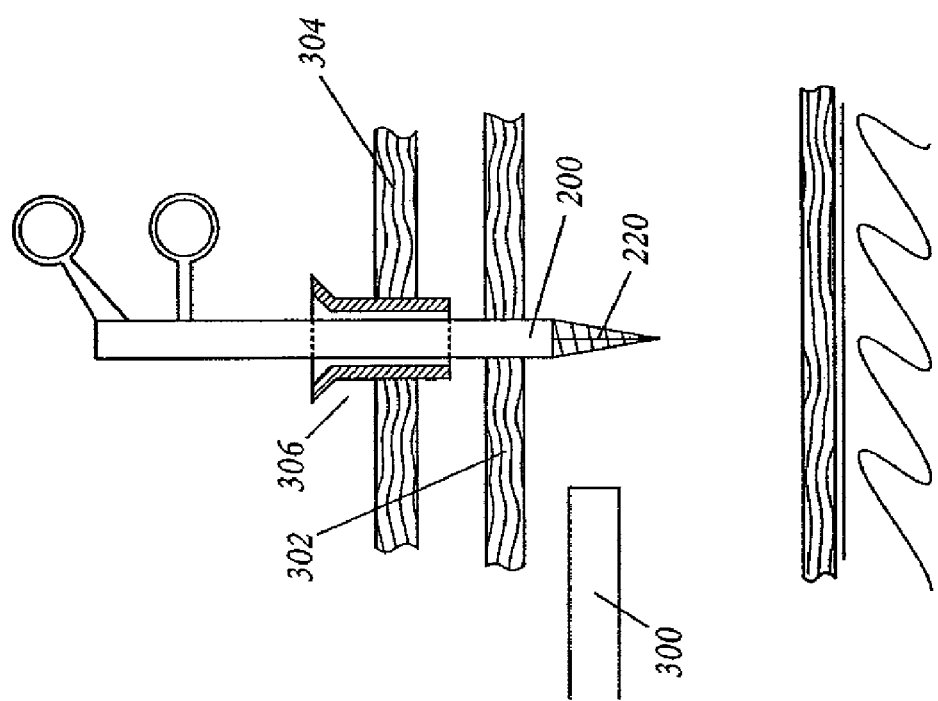
FIG. 6A illustrates the first step in one embodiment of a method of reducing the volume of the stomach. Shown is a side sectional view of a patient's abdomen with the instrument of FIG. 4 inserted into the patient's abdomen through a laparoscopic port.

FIG. 6A depicts the initial step of a preferred embodiment of a surgical method to implant the transgastric fastening assembly. The first part of the procedure involves entering the stomach with an endoscope 300 and insulating the stomach with a gas. When insufflated, the anterior wall of the stomach 302 is pushed toward the anterior abdominal wall 304 to create a potential space. After insufflation of the stomach, an incision is made in the skin and a standard laparoscopic port 306 is placed through the anterior abdominal wall 304 to a position wherein the distal end is in the potential space between the abdominal wall 304 and the anterior wall of stomach 302. The laparoscopic port can be a radially dilating type port or similar port known in the art.

A particularly advantageous port is one which allows visualization of the individual abdominal layers as it is being pushed through the abdominal wall (well known to those skilled in the art). Use of such a port allows the surgeon to "see" the different layers of the abdominal wall from within the trocar (using a standard laparoscopic camera) as the trocar is advanced through the abdominal wall. The endoscopic light inside the stomach will be "seen" by the surgeon as the port approaches the inner layers of the abdominal wall because the endoscopic light source transilluminates through the layers of the stomach wall and inner layers of the abdominal wall. Such visualization is advantageous if the patient has a very thick abdominal wall (e.g. in a morbidly obese patient) because the surgeon needs to ensure that another organ (e.g. the colon) is not draped between the stomach and the posterior wall of the abdomen.

The tissue grasping instrument 200 of FIG. 4A is inserted through the port 306 with the jaws 220 in the closed position (with or without a needle projecting in front of the instrument) and is passed through the anterior wall of the stomach 302. When the jaws of the instrument are closed, the jaws define a sharp, dilating, and/or cutting configuration which can more easily advance through the stomach wall.

FIG. 6B depicts the next step in a preferred method. The jaws of instrument 200 are used to grasp the posterior wall of the stomach 314. The posterior wall of the stomach 314 is lifted away from the retroperitoneum 316, allowing for access to the potential space of the lesser peritoneal sac 320. A needle 232, such as a Veress needle (well-known in the art, a Veress needle allows for easy and safe access into and between two serosal layers), is inserted through the central channel 230 of the instrument and passed through the posterior wall of the stomach 314 into the potential space of the lesser peritoneal sac 320. The potential space of the lesser peritoneal sac 320 is expanded by injection of a gas, such as carbon dioxide, through the needle 232. In other embodiments, the potential space is expanded using a liquid, gel, or foam. Alternatively, the space can be expanded using a balloon or other space expanding or space filling device; alternatively, a surgical instrument (e.g. electrocautery and/or blunt ended grasper, etc.) can be used in place of a needle to access the lesser peritoneum or to expand the potential space of the retroperitoneum 320. Preferably, the expanded space of the lesser peritoneal sac can extend from the angle of His at the gastroesophageal junction to the pylorus.

In an alternative embodiment, the space is not expanded before the posterior anchor is placed. For example, in an embodiment where an inflatable posterior anchor is used, the potential space can be expanded by the anchor itself as it is inflated to its deployed configuration.

Figure 6D:
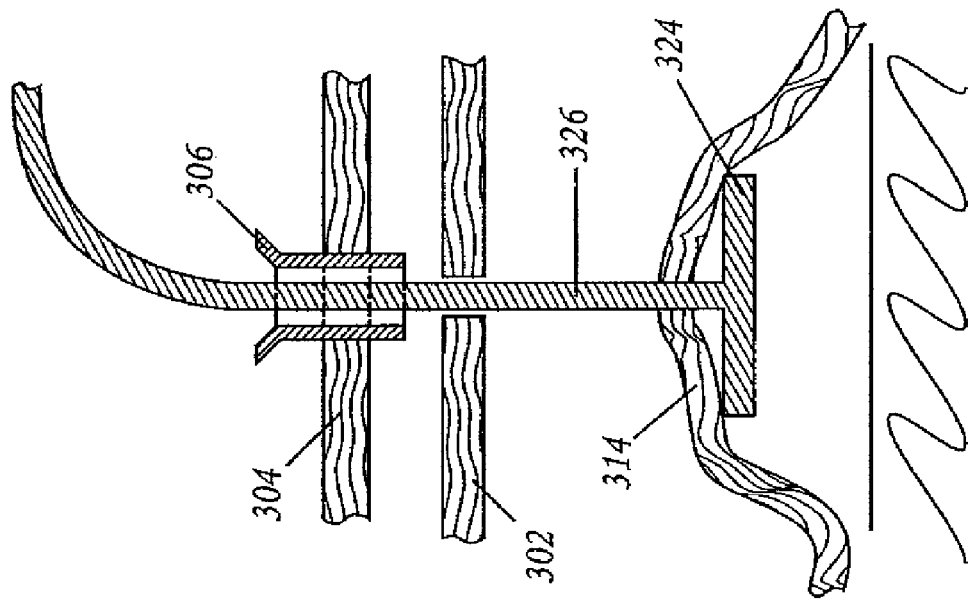
FIG. 6D illustrates the next step in one embodiment of a method of reducing the volume of the stomach. Shown is a side sectional view of a patient's abdomen with a posterior anchor and connector deployed in the expanded potential space of the lesser peritoneal sac, with the connector passing out of the patient's abdomen through a laparoscopic port.
Figure 6C:
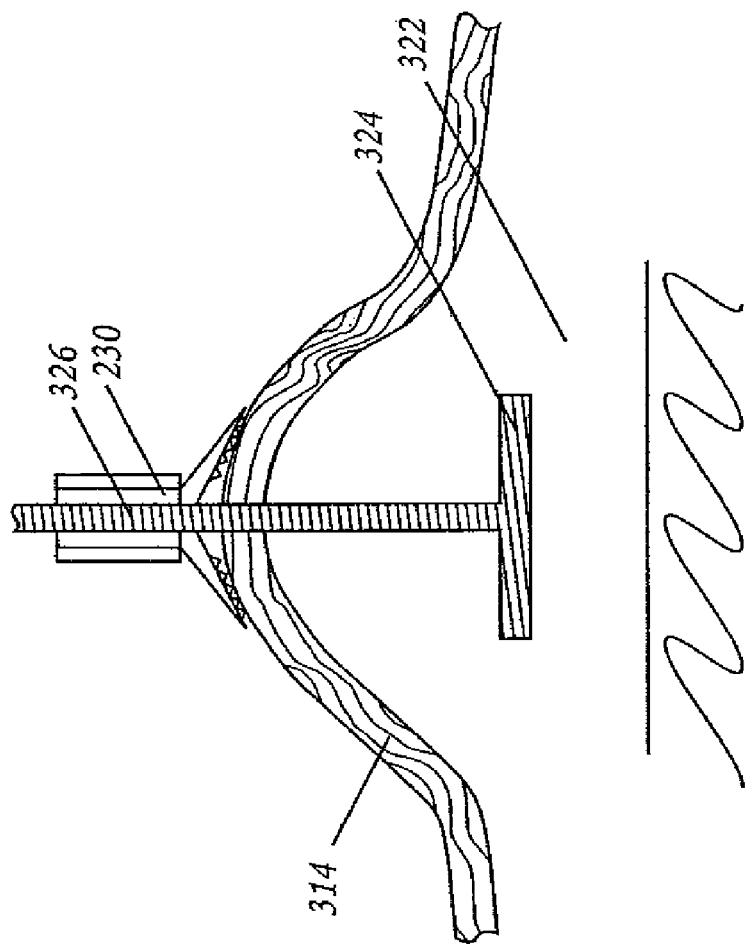
FIG. 6C illustrates the next step in one embodiment of a method of reducing the volume of the stomach. Shown is a side sectional view of a patient's abdomen with the instrument of FIG. 4 grasping the posterior wall of the stomach and a posterior anchor and connector deployed in the expanded potential space of the lesser peritoneal sac.

FIG. 6C depicts the next step in a preferred embodiment. With a direct path from outside the patient to the lesser peritoneal sac 322, the needle 232 is withdrawn from the instrument 200. An optional dilation step can be performed at this stage in the procedure using a device such as a radially dilating sheath (e.g. InnerDyne STEP™ system; Sunnyvale, Calif.) inserted through the central channel 230 of the instrument. The dilating device expands the opening in the posterior wall of the stomach in such a way that the opening contracts down to a lesser profile after dilation. A posterior anchor 324 and connector 326, such as those depicted in FIGS. 1B, 1E or preferably 1F, in its reduced profile configuration, is passed through the central channel 230 of the instrument, through the posterior wall of the stomach 314, and deployed in the lesser peritoneal sac 322 as shown in FIG. 6C. Where the optional dilation step is performed, the posterior anchor 324 is passed through the dilating sheath. The connector 326 is preferably of sufficient length to pass from inside the lesser peritoneal sac 322 through the central channel 230 of the instrument and out of the patient's body. FIG. 6D depicts the deployed posterior anchor 324 and connector 326 after the grasping instrument is withdrawn from the patient and tension is applied to connector 326 to pull the posterior anchor 324 against the posterior wall of the stomach 314.

Figure 7A:
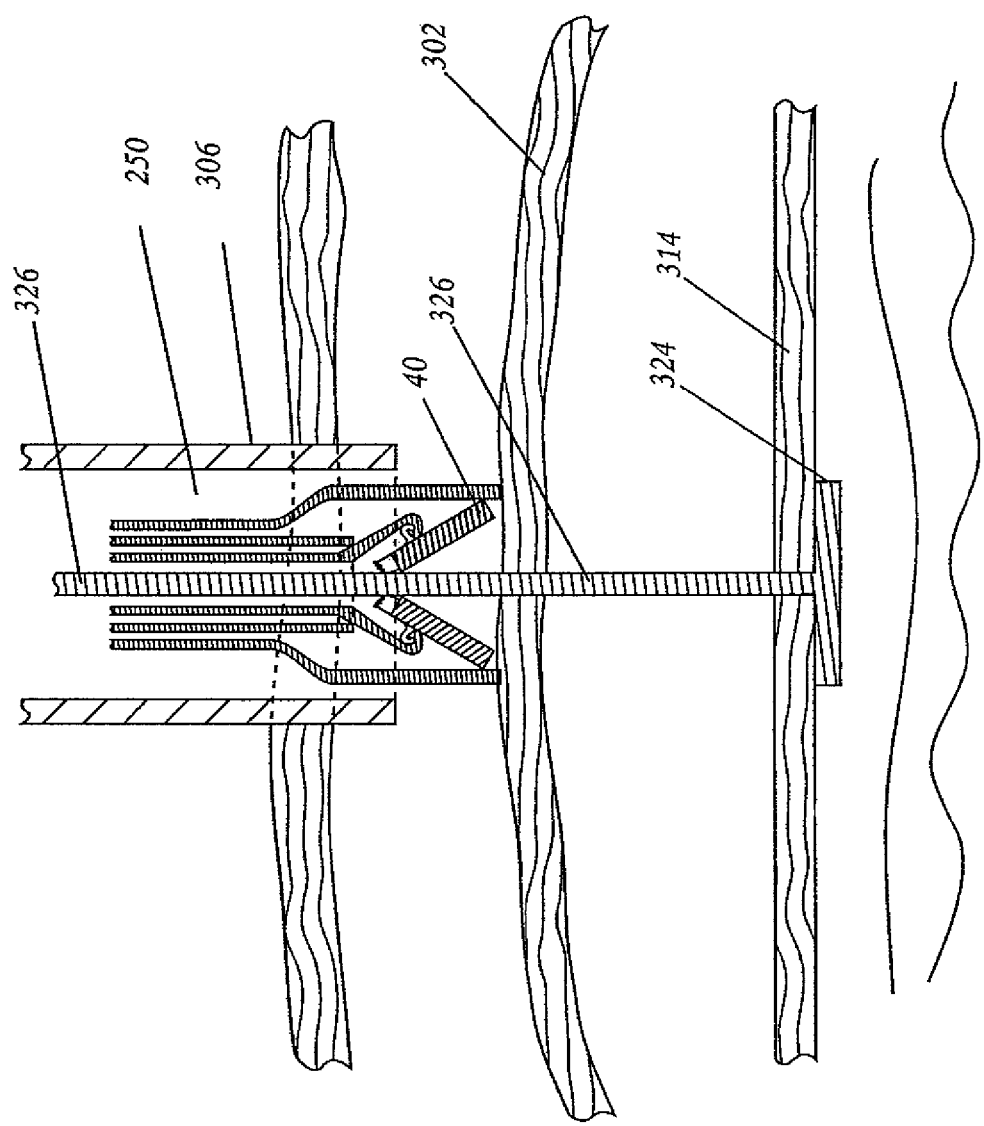
FIG. 7A illustrates the next step in one embodiment of a method of reducing the volume of the stomach. Shown is a side sectional view of a patient's abdomen with the instrument of FIG. 5C placing an anterior anchor in the patient's abdomen adjacent to the anterior wall of the stomach.

FIG. 7A illustrates the next step in the embodiment. The connector 326 is inserted through the hole or other passageway in an anterior anchor 40 of FIG. 5C, and the anchor implantation instrument 250 of FIGS. 5A, 5B and 5C is used to slide the anchor 40 through the laparoscopic port 306 into the abdomen of the patient. The anterior 302 and posterior 314 walls of the stomach are urged together, either by using the anchor implantation instrument 250 to urge the anterior wall 302 toward the posterior wall 314, or by pulling on the connector 326 and posterior anchor 324 to urge the posterior wall 302 of the stomach toward the anterior wall 314, or by a combination of the two methods. Once the anterior anchor 40 is in the desired position, the anterior anchor 40 is placed in its deployed configuration by manipulating the anchor implantation instrument 250 as described above.

In a preferred embodiment, the inflatable anterior anchor of FIGS. 2G-2I is used, and the use of the implantation instrument of FIG. 5C is optional. After the anterior anchor is in the desired position, the anterior anchor is inflated with a filling substance through the inflation tube until it is in its deployed configuration. The gripping elements 67 and teeth 68 are thus engaged against the connector 326. The anchor implantation device 250 can then be withdrawn from the patient's abdomen.

With the transgastric fastening assembly complete, the surgeon can examine the resulting configuration of the stomach using an endoscope. If the anterior anchor is not in the desired location, its placement along the connector can be adjusted as described above. Alternatively, in another embodiment, the anterior anchor can be urged closer to the posterior anchor simply by pushing it along the connector without using the implantation device to capture the anchor and deform it into its reduced profile configuration.

In the preferred embodiment, the anterior anchor can be deflated, allowing the anterior anchor to be repositioned, and then reinflated to engage the connector. FIG. 7B illustrates the transgastric fastening assembly with the anterior anchor 40 in its deployed configuration on the connector 326 and the anchor implantation instrument removed from the patient's abdomen. The anterior 302 and posterior walls 314 of the stomach have been urged closer together by the transgastric fastening assembly. Whether the walls of the stomach are urged into contact or not is determined by the surgeon.

FIG. 7C depicts the transgastric fastening assembly in its final configuration after deployment. Once the surgeon is satisfied that the transgastric fastening assembly is properly placed, a cutting implement, well-known to those of skill in the art, is inserted through the laparoscopic port and the connector 326 is cut, preferably flush to the anterior anchor 40. In the preferred embodiment, where inflatable anchors are used, the hollow connector and inflation tube are sealed prior to, or as a result of, cutting, preventing anchor deflation. Alternatively, if a filling substance which hardens with time is used, it may not be necessary to seal the connector or inflation tube prior to cutting if the filling substance is sufficiently hard or viscous such that it will not leak from the connector or inflation tube.

When more than one transgastric fastening assembly is to be implanted, it is preferred to insert all of the posterior anchors and connectors before attaching any anterior anchors, This is in contrast to attempting to place one complete transgastric fastening assembly and then subsequent assemblies. While possible, if one were to place entire fastening assemblies in series, each successive assembly would be more difficult to place because the volume of the stomach would be progressively reduced resulting in more difficult visualization each time.

Figure 8A:
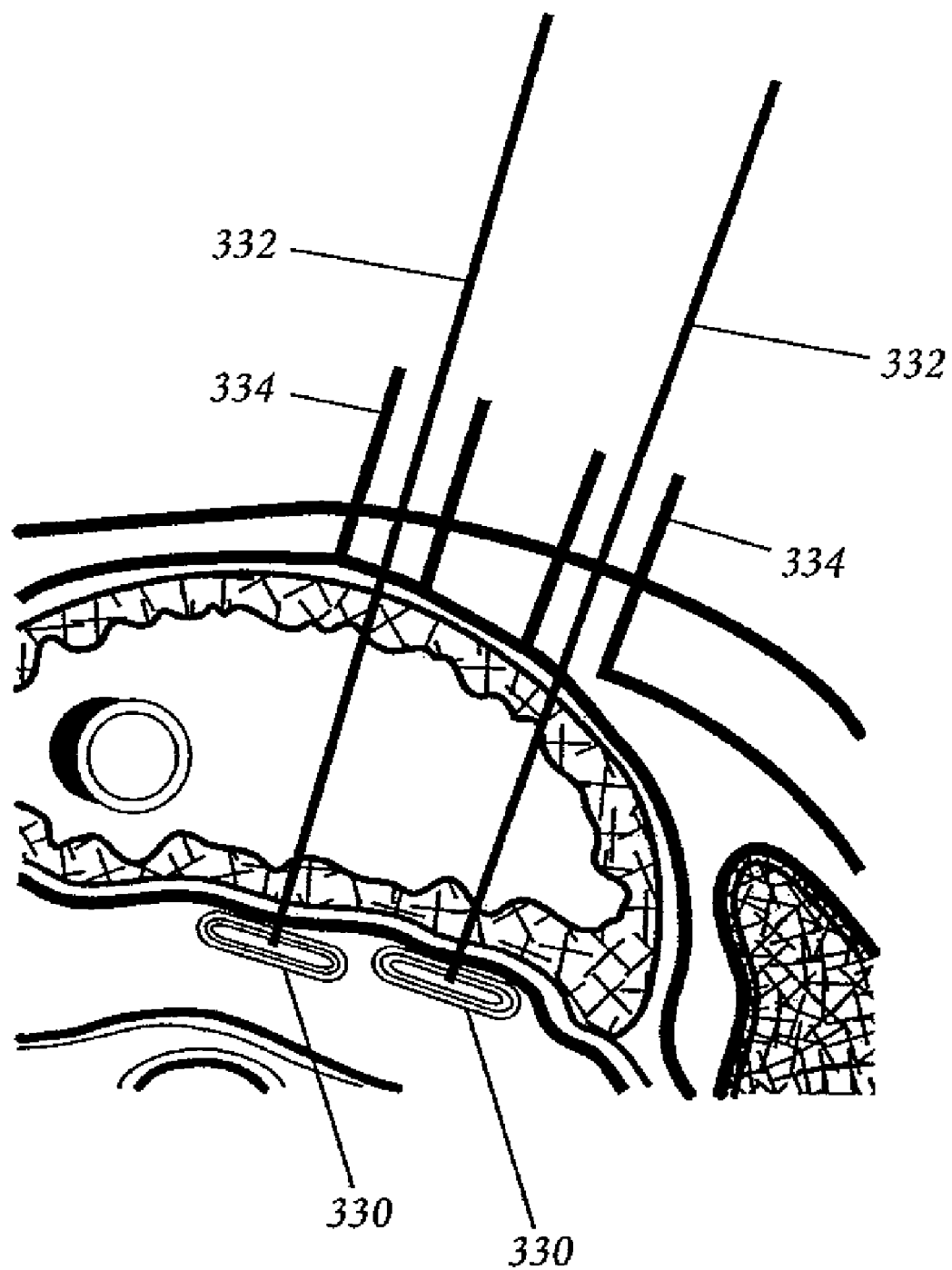
FIG. 8A illustrates an embodiment of a method of reducing the volume of the stomach. Shown is a side sectional view of a patient's abdomen after two posterior anchors and connectors have been deployed adjacent to the posterior wall of the stomach, with the connectors passing out of the patient's abdomen through laparoscopic ports.

FIG. 8A depicts an embodiment in which two posterior anchors 330 and connectors 332 are deployed in the expanded lesser peritoneal sac. In this embodiment, there is one laparoscopic port 334 for each connector 332. Alternatively, there may be more fasteners placed than incisions and laparoscopic ports. Depending on how far apart the fasteners are placed, a given laparoscopic port can be used to implant a plurality of transgastric implants. This can be accomplished because there is significant mobility of the stomach and/or abdominal wall which allows for different points along the anterior wall of the stomach to be accessed without having to create another hole through the abdominal wall.

Figure 8B:
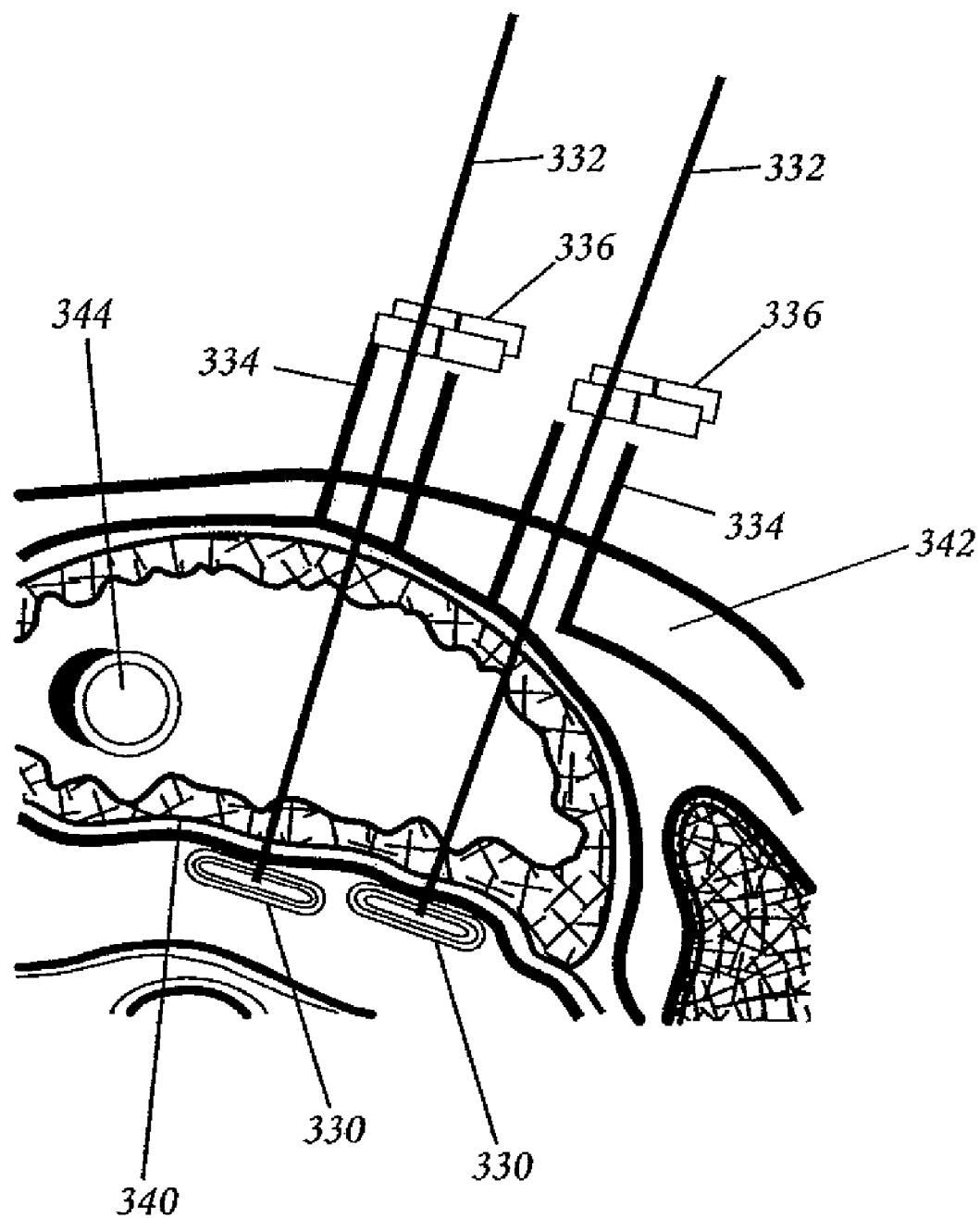
FIG. 8B shows the connectors of FIG. 8A with clamps placed on the connectors outside the patient's body to temporarily hold the connectors in a test position.

When it is desired to place more than one set of transgastric assemblies and in particular when the assemblies are placed concurrently rather than sequentially, the surgeon is afforded the opportunity to test (e.g measuring stomach volume, resistance to flow, assessing mucosal integrity, etc.) varying tensions on one or more of the fastening assemblies, all under endoscopic inspection. After the desired number of posterior anchors and connectors are deployed in the patient, the configuration of the stomach can be tested by applying tension to the connectors. FIG. 8B depicts temporary clamps 336 which sit on top of the ports 334. Connectors 332 can be pulled from outside the abdomen to urge the posterior wall of the stomach 340 toward the anterior abdominal wall 342. One or more clamps 336 can then be closed to hold the stomach in a test position. To determine if the posterior anchors 330 are in the desired location, an endoscope 344 can be used to view the configuration and the tension that the stomach will endure after the anterior anchors are placed.

In an alternative embodiment, the stomach is fastened to the abdominal wall rather than there being a free space between the anterior gastric wall and the peritoneum of the abdominal wall. The initial steps are as discussed above. After the posterior anchors are placed, their position can be tested as depicted in FIG. 8B to simulate the configuration after the anterior fastener is placed. Next, the outer laparoscopic port is pulled back so that the anchor deploying instrument directly contacts and sits within the tissues of the muscular abdominal wall. Once the outer laparoscopic port is pulled back, the anterior anchor can be deployed within the abdominal wall musculature and the connector can be cut flush with the anterior fastener. In an embodiment where the inflatable anterior anchor is used, after the anterior anchor is deployed within the abdominal wall musculature, the inflation tube is cut, preferably flush with the anterior anchor.

Reversal of the Gastric Volume Reduction Procedure

The connector of a preferred embodiment of the deployed transgastric fastening assembly, as illustrated in FIG. 7C, can be cut at a point between the anterior and posterior anchors, which results in reversal of the gastric volume reduction. The connector is preferably made to resist corrosion from stomach acid, but is able to be cut by a cutting implement advanced through an endoscope into the stomach. Materials suitable to prevent corrosion and yet allow cutting include plastics such as polyurethane, silicone elastomer, polypropylene, PTFE, PVDF, or polyester, metals and metal alloys such as stainless steel, nickel-titanium, titanium, cobalt-chromium, etc. Once the connector is cut, the walls of the stomach are free to move away from one another, thereby reversing the procedure. Reversal of the procedure can occur at any time (days to years) after the procedure. In a preferred embodiment, the anchors remain in the gastric wall permanently even after the connector is cut or otherwise divided. Alternatively, the anchors can in part or in whole be manufactured from a bioabsorbable material such that the anchors will eventually be absorbed by the body. In the case of bioabsorbable anchors, it is preferable to have a connector which is at least in part bioabsorbable. In another embodiment, substantially all of the elements of the transgastric fastening assembly are made of bioabsorbable materials, with the intent that over the desired period of time, the entire assembly will be absorbed by the body, reversing the procedure without any additional actions required by a doctor.

Even if there is some degree of fusion between the mucosa around the connector at the region of the assembly, once the connector is cut or absorbed, the walls will tend to move apart over time. Alternatively, a balloon or other dissection device is introduced through an endoscope and used to separate the walls of the stomach at the point of fusion.

Treatment of Disease Conditions

Figure 9:
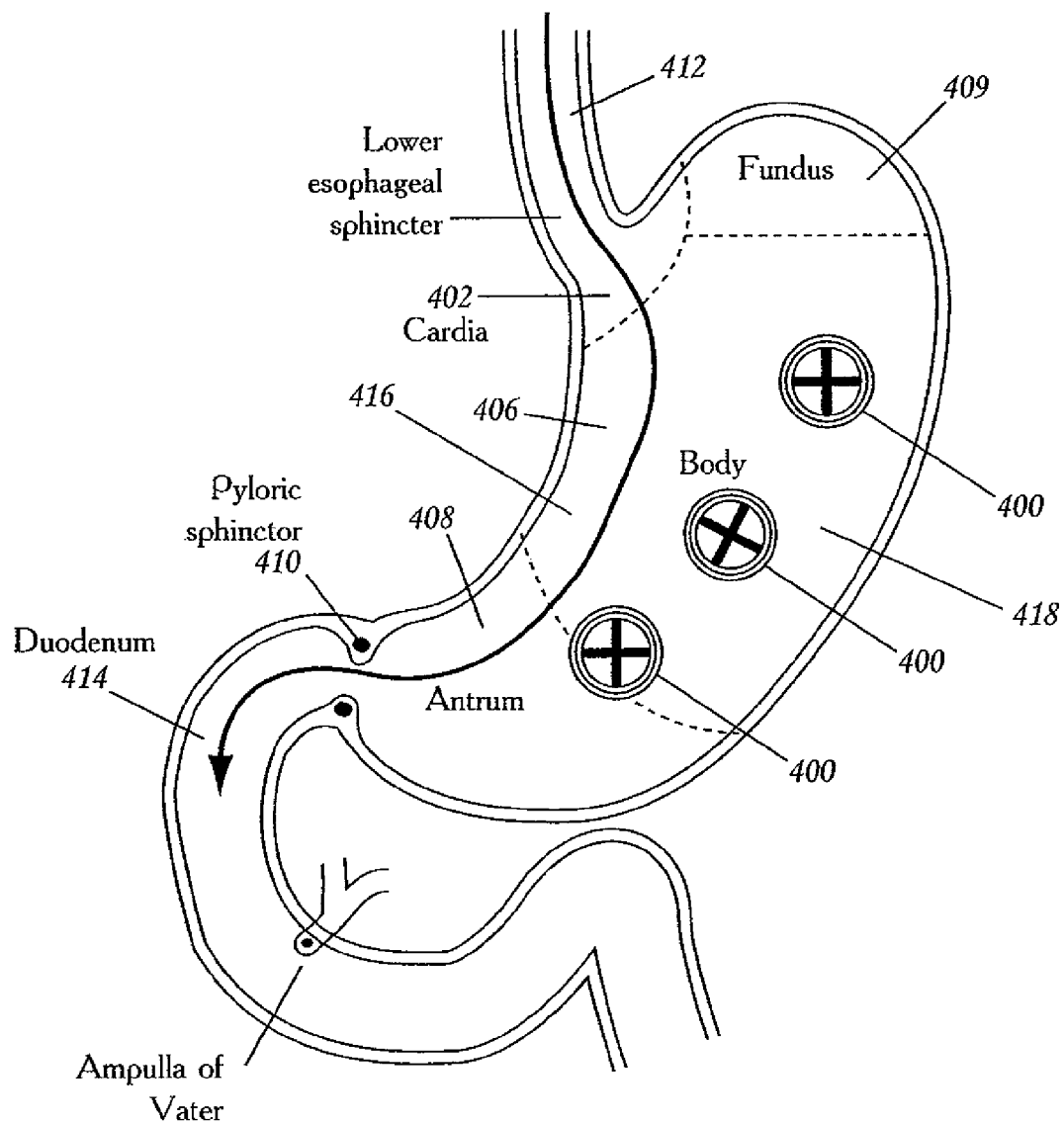
FIG. 9 is a perspective view showing three transgastric fastening assemblies deployed in a patient's stomach.

The devices, methods and instruments disclosed above can be used to treat obesity and other diseases involving the gastrointestinal tract, such as gastroesophageal reflux disease (GERD). FIG. 9 depicts three transgastric fastening assemblies 400 deployed in the stomach. The dashed lines represent boundaries of the divisions of the stomach: the cardia of the stomach 402, the fundus of the stomach 404, the body of the stomach 406, the antrum of the stomach 408, and the pyloric sphincter 410. In a preferred embodiment, the fastening assemblies are not implanted in the antrum 408 in order to maintain the normal digestion process of the stomach. Normal digestion occurs in the antrum which precedes passage of food into the duodenum. In stopping short of the antrum 408, the implants replicate the degree of volume reduction of the M&M procedure.

Food ingested by the patient follows a physiologic pathway for digestion depicted by the arrow in FIG. 9. It travels through the esophagus 412 and enters the cardia of the stomach 402. The food is digested in the stomach and pushed toward the duodenum 414 as chyme for further digestion. The preserved antrum 408 will allow for relatively physiologic digestion and emptying into the duodenum 414 akin to the M&M procedure. With transgastric fastening assemblies 400 in place, food which leaves the esophagus 412 and enters the stomach, results in increased wall tension on the lesser curvature of the stomach 416 as the greater curvature of the stomach 418 will be restricted from the food pathway. The path of least resistance will be the path toward the pylorus 410 and duodenum 414. The increased wall tension of the stomach will result in a feeling of satiety in the patient, leading to decreased food intake and weight loss. Although three assemblies are shown in FIG. 9, there may be as few as one or as many as ten depending on the degree of volume reduction desired. Such flexibility in number of devices as well as the ability of the surgeon to tune the tension between the anterior and posterior fasteners is advantageous. Such flexibility may enable, for example, reversal of a few fasteners rather than all the fasteners, such that the volume reduction procedure is partially reversed.

In another embodiment, a transgastric fastening assembly is placed in the antrum 408 or the region just proximal to the pyloric sphincter 410 if deemed necessary by the gastroenterologist and/or surgeon. Such a configuration would not reduce the volume of the stomach but would cause a feeling of fullness similar to a gastric outlet obstruction, leading to decreased food intake and weight loss. The fasteners in this region can also conduct a current to electrically stimulate the stomach to simulate satiety.

In another embodiment, a transgastric fastening assembly may be required at the region of the cardia 402 to treat morbid obesity in a similar manner to that utilized with the LAP-BAND™. In this embodiment, the transgastric fastening assembly is not utilized to reduce the volume of the stomach, but to create a restriction to the inflow of food.

In another embodiment, the surgeon or gastroenterologist may choose to treat a disease such as gastroesophageal reflux disease (GERD) with a transgastric fastening assembly in the cardia region. Such a configuration would maintain the position of the GE junction in the abdomen and potentially great a barrier resistance to reflux contents.

In another embodiment, the disclosed method in combination with the transgastric fastening assemblies can be adapted to attach a gastrointestinal organ to the abdominal wall which in addition to reducing volume can also create a kink in the organ. The kink would cause a resistance barrier (in addition to volume reduction) to gastrointestinal contents, and can be useful to treat reflux disease or morbid obesity.

Such a kink would also fix the gastrointestinal region to the abdominal wall can also maintain the reduction of a hiatal hernia in the abdominal compartment (e.g. in reflux disease). A major component of reflux disease is a hiatal hernia in which the gastroesophageal junction freely slides from the abdomen to the mediastinum. A percutaneously placed suture or anchor in the region of the gastric cardia and/or fundus can tether the junction to the abdominal wall and confine the junction to the abdomen.

In other embodiments, the devices and methods of this invention can assist in the implantation of devices such as stents, meshes, stitches, or tubes in the gastrointestinal tract. The major technical difficulty encountered in placing stents, tubes, and meshes inside the lumen of the gastrointestinal tract is that they tend to migrate because the walls of such devices do not adhere to slippery mucosa. A transgastric or transintestinal fastener, implanted with the current instrumentation would solve this problem. Such a method would be particularly useful in the attachment of the stent part of the stent-sleeve system outlined in patent application WO 04049982, or the mesh of patent application WO03086247A1. In another example, devices such as those disclosed in U.S. Pat. No. 6,773,441 attempt to place an endoscopic stitch to tether the cardia of the stomach to the fundus to treat reflux disease. Such stitches are tenuous in the long term because they do not necessarily penetrate the serosa. Even if the stitches penetrate the serosa, they tend to erode through the wall with time because of their thin profile and an inability of the endoscopic operator to control tension on the suture when it is placed. With the methods and devices of this invention, such an endoscopic suture can be buttressed with a percutaneously placed fastener.

Other Uses for the Disclosed Devices, Instruments, and Methods

Although the described methods are focused on the implantation of transgastric fastening assemblies to reduce the volume of the stomach, the methods and devices can easily be expanded to the percutaneous placement of other types of devices such as neurostimulators, gastric muscle stimulators, gastric balloons, bulking devices inside the wall of a gastrointestinal organ, devices placed in the lesser peritoneal sac along the autonomic nerve plexus, along the vagus nerve, on parts of the diaphragm, or placed on or along the pancreas.

In some embodiments, other devices are implanted using the described methods to place devices inside or outside the stomach; inside or outside the lesser sac of the peritoneum; inside or beside a structure within the retroperitoneum; inside, beside, or outside the duodenum, pylorus, or gastroesophageal junction. Implanted devices include but are not limited to the anchor devices and transgastric fastening assemblies described above, neuromodulators, direct muscle stimulators, stents, meshes, stent-grafts, stitches, and bulk forming agents.

In one such embodiment, a transgastric fastening assembly serves to reduce the volume of the stomach as well as provide for electrical stimulation. In this embodiment, an electrical signal runs through electrodes in the transgastric fastener assembly to alter the contraction patterns of the stomach or to electrically stimulate a feeling of satiety as well as reduce the volume of the stomach. Thus, fastener assemblies of the present invention can become electrodes which are useful, for example, for gastric electrical stimulation. Methods and devices of this invention can also be used to place sutures in the stomach or pylorus to treat reflux disease. Such suturing would be facilitated by the placement of multiple ports through the walls of the stomach; this would be highly beneficial over current fully endoscopic methods of placing sutures. Any of these methods and devices could be used in combination with or in place of the transgastric fastening assemblies to induce weight loss in a patient.

Figure 10B:
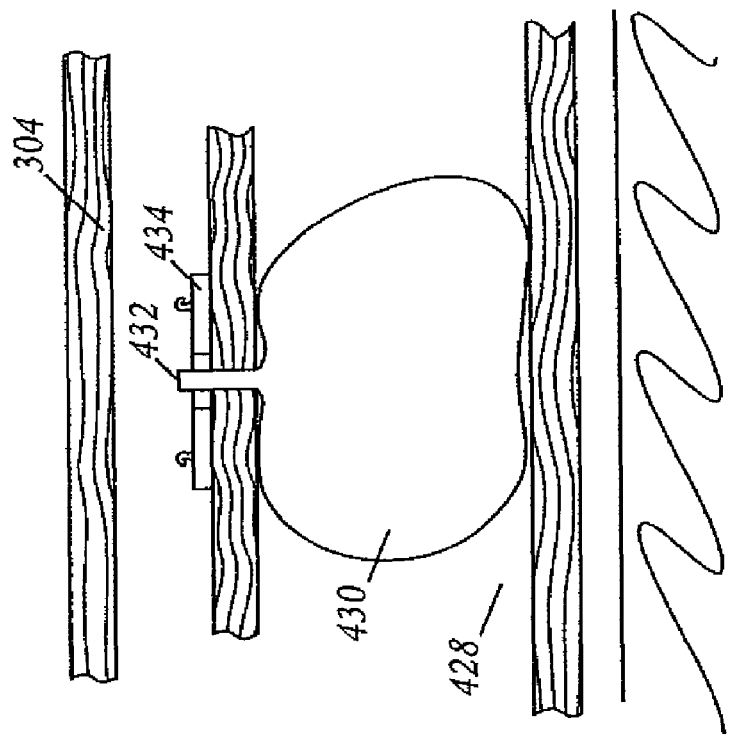
FIG. 10B illustrates one embodiment of a method for deploying a volume displacing device in the stomach. Shown is a side sectional view of a patient's abdomen with the balloon anchor in its deployed position, held in place by an anterior anchor.
Figure 10A:
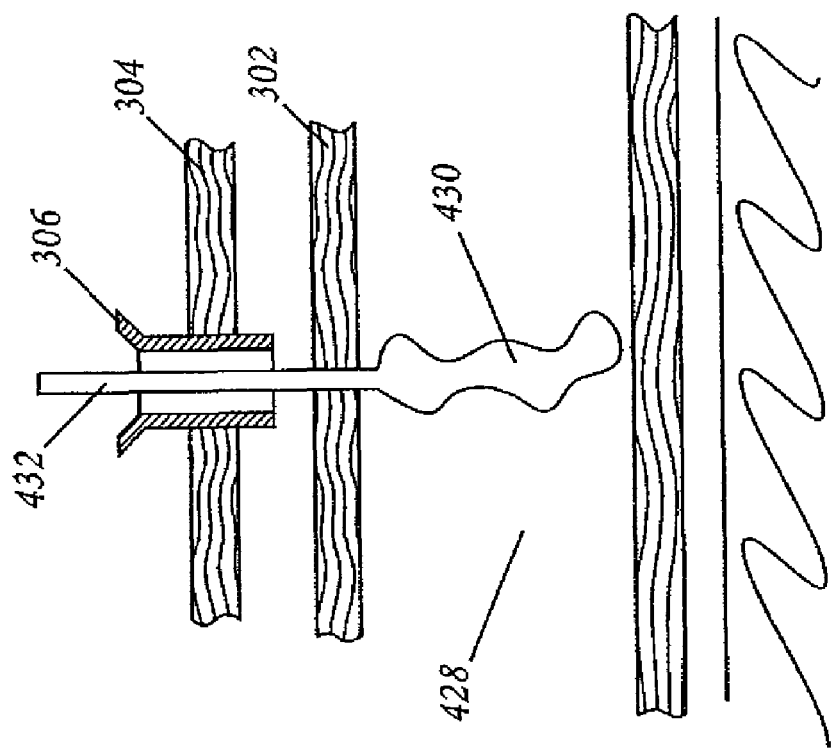
FIG. 10A illustrates one embodiment of a method for deploying a volume displacing device in the stomach. Shown is a side sectional view of a patient's abdomen after an uninflated balloon anchor has been inserted inside the patient's stomach with a connector passing out of the stomach, through the anterior stomach wall, and a laparoscopic port.

In other embodiments, the novel methods, implantation devices, and fasteners of this invention are used to implant devices in one wall of a gastrointestinal organ without volume reduction. In one example of such an embodiment, illustrated in FIGS. 10A and 10B, a balloon-like device is deployed in the stomach to displace volume rather than to reduce volume from the outside. The balloon 430 is the equivalent of the posterior anchors in the above embodiments. In this embodiment, after initial insufflation of the stomach and placement of a laparoscopic port 306 in the abdominal wall 304, an instrument is used to penetrate only the anterior wall of the stomach 302 and place an inflatable intragastric balloon 430. Inflation is achieved through connector 432 and the balloon is placed within the interior of the stomach 428, as illustrated in FIG. 10A. When inflated, the balloon 430 is preferably spherical in shape such that it occupies a portion of the stomach volume when inflated. In the embodiment shown, the connector also acts as the inflation tube for inflating the intragastric balloon. In another embodiment, there is a separate inflation tube in addition to the connector. As discussed above, a valve can be located between the anchor and the connector, or alternatively outside the patient. Preferably after the intragastric balloon is inflated, an anterior anchor 434 is deployed on the connector 432 as described previously, the connector is cut, preferably flush with the anterior anchor, and the laparoscopic port is removed, as shown in FIG. 10B. In the preferred embodiment where an inflatable anterior anchor 434 is used, the inflation tube is also cut, preferably flush with the anterior anchor.

Alternative Implantation Techniques

Although the methods described in this disclosure focus on a percutaneous surgical procedure where general anesthesia and paralysis are not used, it is conceivable that the surgeon may want to use general anesthesia and paralysis. Such may be the case when the adhesions behind the stomach are severe and it will be safer to perform a standard laparoscopic procedure to implant the devices of this invention. In such a case, the percutaneous instruments and implants described in this invention will be used, but the surgeon will additionally have the advantage of laparoscopic instrumentation and tools which can free the posterior gastric wall from the retroperitoneum under direct visualization.

It is also possible that a part of, or the entire procedure is performed under for example with a fluoroscope, MRI, CAT scan, or ultrasound, in which the structures behind the stomach are can be visualized.

Although the present invention has been described in the context of certain preferred or illustrative embodiments, it should be understood that the scope of the exclusive right granted by this patent is not limited to those embodiments, but instead is the fill lawful scope of the appended claims.

What is claimed is:

1. A system for treating a condition in a human patient by modifying the tissue or the flow in an anatomical structure in the body of the human, causing a change in a human condition, said system comprising:
   an anchor device comprising a first anchor, a second anchor, and a connector that extends between said first and said second anchors;

and, wherein at least one of said first and said second anchors comprises a mesh material.

2. The system of claim 1 wherein the anatomical structure is a luminal structure and at least one of said first and second anchors is configured to engage or rest on a surface of the luminal structure within said human patient.

3. The system of claim 1, wherein said connector comprises a suture.

4. The system of claim 1, wherein said connector can be shortened after at least one of said anchors has been implanted.

5. The system of claim 1, further comprising a delivery device for delivering said anchor device into the body of the human patient body.

6. The system of claim 5, wherein the delivery device comprises an elongate member having a lumen;
wherein said anchor device is initially contained within the lumen of said elongate member; and
wherein said anchor device is moveable through the lumen and thence out of the lumen.

7. The device of claim 5, wherein said anatomical structure is a stomach.

8. The device of claim 1 wherein said anatomical structure is a stomach.

9. The device of claim 8 wherein said connector is a suture.

10. The system of claim 1 further comprising an expandable device attached to at least one of: the first anchor, the second anchor, and the connector.

11. The system of claim 10 wherein the anatomical structure is a stomach.

12. The system of claim 10 wherein the expandable device is fluid fillable.

13. The system of claim 12 wherein the expandable device is further adapted to press on the stomach when it is filled with fluid.

14. The system of claim 1 wherein one of the first or second anchor is expandable with fluid and is configured to press on the stomach from the outside, the other of the first or second anchor comprises the mesh, the anatomical structure is the stomach, and the connector is a suture.

15. The system of claim 1 wherein at least one of the anchors is attachable to the abdominal wall.

16. The system of claim 15 wherein the anchoring device is moveable through a lumen adapted to traverse the abdominal wall and the connector between the anchors is adapted to apply tension to the anchors, through said lumen; and, one of the anchors is finable with a fluid and compress a stomach from the outside.

17. A system for treating a condition in a human patient by modifying the tissue or the flow in an anatomical structure in the body of the human patient, causing a change in a human condition, said system comprising:

an anchor device comprising a first anchor, a second anchor, and a connector that extends between said first and said second anchors;

a delivery device for delivering said anchor device into the body of the human patient wherein said delivery device comprises an elongate member having a lumen and wherein said anchor device is initially contained within the lumen of said elongate member and wherein said anchor device is moveable through the lumen and thence out of the lumen;

and, wherein said elongate member is configured to be advanced into a luminal structure in said human patient, and then into an anatomical structure adjacent to said luminal structure.

18. The system of claim 17, wherein said connector is elastic.

19. The system of claim 17 wherein said anchor device comprises a material which creates a fibrous reaction in a tissue.

20. The system of claim 17 wherein said connector is a suture like material.

21. The system of claim 17 wherein said luminal structure is a stomach.

22. The system of claim 17 wherein said anchor device comprises a T shape.

23. The system of claim 17 wherein the connector and at least one anchor is a continuous structure.

24. The system of claim 17 wherein at least one anchor comprises a shape memory material.

25. The system of claim 17 wherein the anchoring device is configured to receive an electrical current.

26. A kit for modifying the volume of an internal organ of a patient comprising:
a first anchor, a second anchor, and a connector wherein said connector comprises an elongate portion having at least one toothed surface;
wherein at least one of said first or said second anchors have a deployed configuration;
wherein said first anchor and said second anchor each have a surface area sufficient to prevent said first anchor and said second anchor from passing through said organ or tissue when in said deployed configuration;
and wherein said connector and said anchors are configured to permit said first anchor and said second anchor to be linked through said connector.

27. The kit of claim 26, further comprising a tensioning instrument configured to urge said first and said second anchor close together when said connector is connected to said first and said second anchors.

* * * * *